US008853394B2

(12) United States Patent
Campbell et al.

(10) Patent No.: US 8,853,394 B2
(45) Date of Patent: Oct. 7, 2014

(54) PHARMACOKINETICALLY IMPROVED COMPOUNDS

(71) Applicant: Surface Logix, Inc., Brighton, MA (US)

(72) Inventors: Stewart Campbell, Framingham, MA (US); David Duffy, Somerville, MA (US); Michael Grogan, Winchester, MA (US); Steven Kates, Needham, MA (US); Emanuele Ostuni, Lexington, MA (US); Olivier Schueller, Arlington, MA (US); Paul Sweetnam, Marblehead, MA (US)

(73) Assignee: Surface Logix, Inc., Brighton, MA (US)

( * ) Notice: Subject to any disclaimer, the term of this patent is extended or adjusted under 35 U.S.C. 154(b) by 0 days.

(21) Appl. No.: 13/708,420

(22) Filed: Dec. 7, 2012

(65) Prior Publication Data

US 2013/0096114 A1    Apr. 18, 2013

Related U.S. Application Data

(63) Continuation of application No. 12/438,504, filed as application No. PCT/US2007/018784 on Aug. 23, 2007, now abandoned.

(60) Provisional application No. 60/840,306, filed on Aug. 24, 2006.

(51) Int. Cl.
| | | |
|---|---|---|
| *C07D 487/04* | (2006.01) | |
| *A61K 31/53* | (2006.01) | |
| *A61P 9/02* | (2006.01) | |
| *A61P 15/10* | (2006.01) | |

(52) U.S. Cl.
CPC .................. *C07D 487/04* (2013.01)
USPC .......................... 544/184; 514/243

(58) Field of Classification Search
USPC .......................... 544/184; 514/243
See application file for complete search history.

(56) References Cited

U.S. PATENT DOCUMENTS

| | | | |
|---|---|---|---|
| 4,631,211 A | 12/1986 | Houghten | |
| 5,143,854 A | 9/1992 | Pirrung | |
| 5,288,514 A | 2/1994 | Ellman | |
| 5,359,115 A | 10/1994 | Campbell et al. | |
| 5,362,899 A | 11/1994 | Campbell | |
| 5,440,016 A | 8/1995 | Biondelle et al. | |
| 5,480,971 A | 1/1996 | Houghten et al. | |
| 6,362,178 B1 | 3/2002 | Niewohner et al. | |
| 6,476,029 B1 | 11/2002 | Niewohner et al. | |
| 6,803,365 B2 | 10/2004 | Niewohner et al. | |
| 8,357,693 B2 * | 1/2013 | Bartolozzi et al. ....... | 514/266.23 |

FOREIGN PATENT DOCUMENTS

| | | |
|---|---|---|
| DE | 198 27 640 A1 | 12/1999 |
| DE | 101 07 639 A1 | 8/2002 |
| WO | 91/07087 | 5/1991 |
| WO | 92/10092 | 6/1992 |
| WO | 93/09668 | 5/1993 |
| WO | 93/20242 | 10/1993 |
| WO | 94/08051 | 4/1994 |
| WO | 99/24433 A1 | 5/1999 |
| WO | 01/80860 | 11/2001 |
| WO | 02/48676 | 6/2002 |
| WO | 03/012392 | 2/2003 |
| WO | 03/018854 | 3/2003 |
| WO | 03/054515 | 7/2003 |
| WO | 03/099194 | 12/2003 |
| WO | 2006/015715 A1 | 2/2006 |
| WO | 2006/089275 A2 | 8/2006 |

OTHER PUBLICATIONS

Dunn, "Synthesis of Commercial Phosphodiesterase(V) Inhibitors." Organic Process Research & Development, Jan. 2005, vol. 9, pp. 88-97.
Bhadra et al. "Pegnology: a Review of PEG-ylated Systems." Pharmazie 57, 2002, pp. 5-29.
Molineux, "Pegylation: Engineering Improved Pharmaceuticals for Enhanced Therapy." Cancer Treatment Reviews 28 (Suppl. A), 2002, pp. 13-16.
Crawford, "Clinical uses of Pegylated Pharmaceutics in Oncology." Cancer Treatment Reviews 28 (Suppl. A), 2002, pp. 7-11.
Yowell et al., "Novel Effects with Polyethylene Glycol Modified Pharmaceuticals." Cancer Treatment Reviews 28 (Suppl. A), 2002, pp. 3-6.
Harris et al., "Pegylation: A Novel Process for Modifying Pharmacokinetics." Clin. Pharmacokinet, vol. 40, No. 7, 2001, pp. 539-551.
Greene et al. "Protective Groups in Organic Synthesis." 2nd Edition, John Wiley & Sons, 1991.
Chapman et al., "Surveying for Surfaces that Resist the Adsorption of Proteins." J. Am. Chem. Soc. 122, 2000, pp. 8303-8304.
Ostuni et al. "A Survey of Structure-Property Relationships of Surfaces that Resist the Adsorption of Protein." Langmuir 17, 2001, pp. 5605-5620.
Holmlin et al., "Zwitterionic SAMs that Resist Nonspecific Adsorption of Protein from Aqueous Buffer." Langmuir 17, 2001, pp. 2841-2850.

(Continued)

Primary Examiner — Venkataraman Balasubramanian
(74) Attorney, Agent, or Firm — Kenyon & Kenyon LLP

(57) ABSTRACT

A compound of formula A having improved non-specific binding characteristics and pharmacokinetic properties is provided:

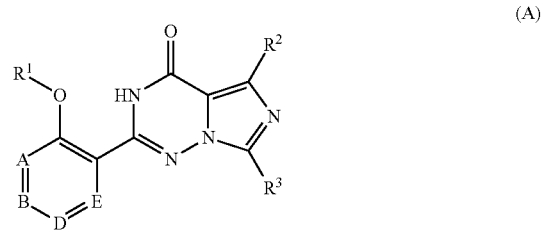

(A)

or a pharmaceutically acceptable salt, stereoisomer, or hydrate thereof.

25 Claims, No Drawings

(56) References Cited

OTHER PUBLICATIONS

Ostuni et al. "Self-Assembled Monolayers that Resist the Adsorption of Proteins and the Adhesion of Bacterial and Mammalian Cells." Langmuir 17, 2001, pp. 6336-6343.

Sasaki et al. "Transcellular Transport of Organic Anions Across a Double-Transfected Madin-Darby Canine Kidney II Cell Monolayer Expressing Both Human Organic Anion-Transporting Polypeptide (OATP2/SLC21A6) and Multidrug Resistance-Associated Protein 2 (MRP2/ABCC2)." The Journal of Biological Chemistry, vol. 277, No. 8, Feb. 22, 2002, pp. 6497-6503.

Berge et al. "Pharmaceutical Salts." Journal of Pharmaceutical Sciences, vol. 66, No. 1, Jan. 1988, pp. 1-19.

Dordunoo et al., "Preformulation Studies on Solid Dispersions Containing Triamterene or Temazepam in Polyethylene Glycols or Gelucire 44/14 for Liquid Filling of Hard Gelatin Capsules." Drug Development and Industrial Pharmacy, vol. 17, No. 12, 1991, pp. 1685-1713.

Sheen et al. "Bioavailability of a Poorly Water-Soluble Drug From Tablet and Solid Dispersion in Humans." Journal of Pharmaceutical Sciences, vol. 80, No. 7, Jul. 1991, pp. 712-714.

Blondelle et al. "Soluble Combinatorial Libraries of Organic, Peptidomimetic and Peptide Diversities." Trends in Analytical Chemistry, vol. 14, No. 2, 1995, pp. 14:83.

Chen et al. "'Analogous' Organic Synthesis of Small-Compound Libraries: Validation of Combinatorial Chemistry in Small-Molecule Synthesis." J. Am. Chem. Soc. 116, 1994, pp. 2661-2662.

Kerr et al. "Encoded Combinatorial Peptide Libraries Containing Non-Natural Amino Acids." J. Am. Chem. Soc. 115, 1993, pp. 2529-2531.

Geysen et al. "Use of Peptide Synthesis to Probe Viral Antigens for Epitopes to a Resolution of a Single Amino Acid." Proc. Natl. Acad. Sci. 81, Jul. 1984, pp. 3998-4002.

Bray et al., "The Simultaneous Multiple Productions of Solution Phase Peptides; Assessment of the Geysen Method of Simultaneous Peptide Synthesis." Tetrahedron Letters, vol. 31, No. 40, 1990, pp. 5811-5814.

Valerio et al. "Synthesis of Peptide Analogues Using the Multipin Peptide Synthesis Method." Analytical Biochemistry 197, 1991, pp. 168-177.

Bray et al. "Gas Phase Cleavage of Peptides from a Solid Support with Ammonia Vapour. Application in Simultaneous Multiple Peptide Synthesis." Tetrahedron Letters, vol. 32, No. 43, 1991, pp. 6163-6166.

Houghten, "General method for the Rapid Solid-Phase Synthesis of Large Numbers of Peptides: Specificity of Antigen-Antibody Interaction at the Level of Individual Amino Acids." Proc. Natl. Acad. Sci. 82, Aug. 1985, pp. 5131-5135.

Dower et al. "Chapter 28. The Search for Molecular Diversity (II): Recombinant and Synthetic Randomized Peptide Libraries." Annual Reports in Medicinal Chemistry 26, 1991, pp. 271-280.

Fodor et al. "Light-Directed Spatially Addressable Parallel Chemical Synthesis." Science, vol. 251, No. 4995, Feb. 15, 1991, pp. 767-773.

Jacobs et al. "Combinatorial Chemistry—Applications of Light-Directed Chemical Synthesis." (1994) Trends in Biotechnology 12, 1994, pp. 19-26.

Gallop et al. "Applications of Combinatorial Technologies to Drug Discovery." Journal of Medicinal Chemistry, vol. 37, No. 9, Apr. 29, 1994, pp. 1233-1251.

Brenner et al. "Encoded Combinatorial Chemistry." Proc. Natl. Acad. Sci. 89, Jun. 1992, pp. 5381-5383.

Needels et al. "Generation and Screening of an Oligonucleotide-Encoded Synthetic Peptide Library." Proc. Natl. Acad. Sci. 90, Nov. 1993, pp. 10700-10704.

Nikolaiev et al. "Peptide-Encoding for Structure Determination of Nonsequenceable Polymers Within Libraries Synthesized and Tested on Solid-Phase Supports." Peptide Research, vol. 6, No. 3, 1993, pp. 161-170.

Patek et al. "Safety-Catch Anchoring Linkage for Synthesis of Peptide Amides by Boc/Fmoc Strategy." Tetrahedron Letters. vol. 32, No. 31, pp. 3891-3894, 1991.

Ohlmeyer et al. "Complex Synthetic Chemical Libraries Indexed with Molecular Tags." Proc. Natl. Acad. Sci. 90, 1993, pp. 10922-10926.

Nestler et al. "A General method for Molecular Tagging of Encoded Combinatorial Chemistry Libraries." J. Org. Chem. 59, 1994, pp. 4723-4724.

Burbaum et al. "A Paradigm for Drug Discovery Employing Encoded Combinatorial Libraries." Proc. Natl. Acad. Sci., 92, Jun. 1995, pp. 6027-6031.

Vippagunta, S.R. et al., "Crystalline solids", Advanced Drug Delivery Reviews (2001), vol. 48, pp. 3-26.

West, A. R., Solid State Chemistry and its Applications, Wiley, New York, 1988, pp. 358 and 365.

Supplementary European Search Report dated Dec. 2, 2012 from EP 07837341.

* cited by examiner

PHARMACOKINETICALLY IMPROVED COMPOUNDS

BACKGROUND OF THE INVENTION

The physiological and clinical effects of inhibitors of cyclic guanosine 3',5'-monophosphate specific phosphodiesterase (cGMP-specific PDE) suggest that such inhibitors have utility in a variety of disease states in which modulation of smooth muscle, renal, hemostatic, inflammatory, and/or endocrine function is desired. Type 5 cGMP-specific phosphodiesterase (PDE5) is the major cGMP hydrolyzing enzyme in vascular smooth muscle. Thus, an inhibitor of PDE5 may be indicated in the restoration or maintenance of endothelial and cardiovascular health and treatment of cardiovascular disorders, including but not limited to hypertension, cerebrovascular disorders, and disorders of the urogenital system, particularly erectile disfunction.

Pharmaceutical products that provide selective inhibition of PDE5 are currently available. Vardenafil, marketed under the trade name Levitra® is a potent and selective inhibitor of PDE5 and is currently indicated for the treatment of erectile dysfunction. There is a present need to improve the pharmacokinetic properties of PDE5 inhibitors.

The development of a new pharmaceutical agent requires careful optimization of the chemical and biological properties of a lead compound. For example, a successful drug candidate must be safe and effective for its intended use. Further, the compound must possess desired pharmacokinetic and pharmacodynamic profiles. This arduous development process usually requires extensive experimentation. In many cases, the process for determining the optimal compound can often require preparation of thousands of structurally similar compounds.

Among the properties that can limit the utility of a potential pharmaceutical agent is the degree to which the compound is complexed to proteins in vivo. If a high percentage of the compound present in vivo is non-specifically bound, for example by components of blood and blood plasma, this leaves only a very small amount of free compound available to tissue to perform its therapeutic function. Thus, binding of the compound to various proteins and other plasma components may require an unacceptably large dosage of compound to achieve the desired therapeutic effect.

Traditional approaches have sought to alter pharmacokinetic properties.

Pegylation, the process of the conjugating or linking of biomolecules and drug delivery systems, e.g. liposomes, proteins, enzymes, drugs, nanoparticles, with polyethylene glycol, is a known method for altering pharmacokinetics by improving the circulating half-life of protein and liposomal pharmaceuticals. (See, Bhadra et al. Pharmazie 2002 January; 5791):5-29) Pegylayted drugs have a large molecular weight polyethylene glycol (PEG) shell around the drug which protects the drug from enzymatic degradation, and allows the drug to cross the gut, i.e. provides oral availability and also acts as a shield to prevent recognition of the pegylated drug by cells of the immune system and protects the drug from renal clearance. (see, Molineux, Cancer Treat Rev. 2002 April, 28 Suppl A:13-16) As a result, pegylated proteins, for example, have improved pharmacokinetics due to decreased hydrolysis and a longer circulating half-life. Anticancer agents have a suboptimal pharmacokinetic profile that requires prolonged or repetitive administration of the drug. Pegylated anticancer agents, e.g. pegfilgrastim, a pegylated filgrastim, have been shown to maintain drug efficacy and patient tolerability that are at least equivalent to those of unmodified filgrastim with only one administration per chemotherapy cycle. (see, Crawford, Cancer Treat Rev. 2002 April; 28 Suppl A:7-11) Pegylated liposomal doxorubicin, another chemotherapeutic agent, has been found to be more effective and less cardiotoxic than the unpegylated or liposome-encapsulated doxorubicin. (See, Crawford, 2002) In addition to improved pharmacokinetics, pegylated drugs permit reduced dosing schedules, e.g. a fixed dose rather than a weight based dose. (See, Yowell and Blackwell, Cancer Treat Rev. 2002 April; 28 Suppl A:3-6) Since the PEG size, its geometry and attachment site of the pegylated therapeutic agent, e.g. proteins, determine the drug pharmacokinetics, therapeutic agents must be designed on a protein-by-protein basis. (See, Harris et al. Clin. Pharmacokinet. 2001, 40(7): 539-551) A shortcoming of pegylated agents is potential reduced drug activity at the target site due to steric hindrance of the large PEG molecule. PEG molecule size is more of a concern in small molecules than with proteins.

SUMMARY OF THE INVENTION

The present invention relates to 2-phenyl substituted imidazotriazinone compounds with a sarcosine functional group having improved non-specific binding characteristics and pharmacokinetic properties. The sarcosine unit serves to decrease protein binding, thereby increasing the amount of free form of the compound. The functional residues which are attached to a compound differ in their chemical structure from the groups used in PEG techniques, e.g. the functional residue may be an ethylene glycol derivative, the functional residues are of a significantly smaller molecular weight, e.g. approximately MW of 100 daltons compared to 5000 daltons or more used in standard pegylation. Accordingly, the chemical or biological activity of compounds comprising the functional residues of the present invention is not altered due to less steric hindrance and greater drug accessibility to the target site(s) of the compound.

A compound of formula A having improved non-specific binding characteristics and pharmacokinetic properties is provided:

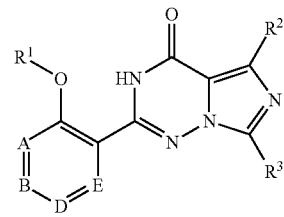

(A)

or pharmaceutically acceptable salt, stereoisomer, or hydrate thereof, wherein $R^1$ is lower alkyl;

$R^2$ is selected from lower alkyl, lower alkenyl and lower alkynyl, wherein the lower alkyl, lower alkenyl, and lower alkynyl may be optionally substituted with one or more halogen, lower alkoxy, hydroxy, CN, $NO_2$, amino, acylamino, amido, carbonyl, and alkylthio;

$R^3$ is selected from lower alkyl, lower alkenyl and lower alkynyl, wherein the lower alkyl, lower alkenyl, and lower alkynyl may be optionally substituted with one or more halogen, lower alkoxy, hydroxy, CN, $NO_2$, amino, acylamino, amido, carbonyl, and alkylthio;

A is N or C—H;

B is N, C—H, C—(SO$_2$—R$^4$), or C—CO—R$^4$;
D is N, C—H, C—(SO$_2$—R$^4$) or C—CO—R$^4$;
E is N or C—H;
   wherein only one of A, B or E may be N, and one of B or D is C—(SO$_2$—R$^4$) or C—CO—R$^4$;
R$^4$ is a group having the formula:
   —NH—R$^{41}$,
   —N(R$^{42}$)(R$^{43}$),

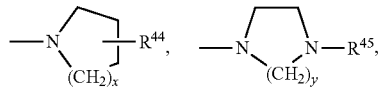

and
   —N(R$^{46}$)$_2$;
R$^{41}$ is selected from C$_3$-C$_6$ alkyl, C$_2$-C$_3$alkyl-OH, —(CH$_2$)$_a$—N(H)(R$^{51}$) and —(CH$_2$)$_a$—N(R$^{52}$)(R$^{53}$);
   R$^{51}$ is selected from alkyl, cycloalkyl, cycloalkenyl, alkyl-O-alkyl, alkyl-O-aryl, alkenyl, alkynyl, aralkyl, aryl and a heterocyclic group;
   R$^{52}$ and R$^{53}$ are taken together with the nitrogen to which they are attached to form a 5- to 7-membered ring which is substituted at a ring carbon with one or two oxo groups and which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group,
   a is 1 to 6;
R$^{42}$ is selected from alkyl, and C$_2$-C$_6$alkyl-O-alkyl;
R$^{43}$ is selected from alkyl, C$_2$-C$_6$alkyl-NH-alkyl, C$_2$-C$_6$alkyl-O-alkyl, alkyl-CO$_2$H, C$_2$-C$_6$alkyl-CH(O-alkyl)(O-alkyl), C$_2$-C$_6$alkyl-CH$_2$(O-alkyl)-alkyl-O-alkyl, —(CH$_2$)$_a$—N(H)(R$^{51}$) and —(CH$_2$)$_a$—N(R$^{52}$)(R$^{53}$);
R$^{44}$ is selected from is selected from the group consisting of —(CH$_2$)$_q$—N(R$^{12}$)(R$^{13}$), —(CH$_2$)$_r$—N(R$^{11}$)—(CH$_2$)$_s$C(O)R$^{14}$, —(CH$_2$)$_q$—C(O)R$^{14}$,
   —(CH$_2$)$_r$—C(O)—(CH$_2$)$_s$OR$^{11}$, —(CH$_2$)$_r$—C(O)—(CH$_2$)$_s$N(R$^{12}$)(R$^{13}$), and
   —(CH$_2$)$_r$O—(CH$_2$)$_s$—C(O)R$^{14}$,
   each R$^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;
   each R$^{12}$ and R$^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or R$^{12}$ and R$^{13}$ may be taken together with the nitrogen to which they are attached foam a 5- to 7-membered ring which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group;
   each R$^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;
   q is 1 to 6:
   r is 0 to 6;
   s is 0 to 6;
R$^{45}$ is selected from is selected from the group consisting of —(CH$_2$)$_v$—N(R$^{25}$)(R$^{26}$), —(CH$_2$)$_v$—N(R$^{21}$)—(CH$_2$)$_w$—C(O)R$^{24}$, —(CH$_2$)$_v$—C(O)R$^{24}$,
   —(CH$_2$)$_t$—C(O)—(CH$_2$)$_w$OR$^{21}$, —(CH$_2$)$_t$—C(O)(CH$_2$)$_w$—N(R$^{22}$)(R$^{23}$),
   —(CH$_2$)$_v$—O—(CH$_2$)$_w$—C(O)R$^{24}$;

each R$^{21}$ is independently selected from H, alkyl, alkyl-O-alkyl, alkyl-O-aryl, alkenyl, alkynyl, cycloalkyl, cycloalkenyl, aralkyl, aryl and a heterocyclic group;
each R$^{22}$ and R$^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or R$^{22}$ and R$^{23}$ may be taken together with the nitrogen to which they are attached form a 5- to 7-membered ring which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group,
each R$^{24}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;
R$^{25}$ and R$^{26}$ taken together with the nitrogen to which they are attached form a 5- to 7-membered ring which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group;
t is 0 to 6;
v is 1 to 6;
w is 0 to 6;
x is 1 or 2;
y is 1 or 2; and
R$^{46}$ are both selected from C$_2$-C$_6$alkyl-OH, and C$_2$-C$_6$alkyl-O—C$_2$-C$_6$alkyl.

The present invention includes pharmaceutical compositions comprising the compounds of the invention and a pharmaceutically acceptable carrier and/or diluents.

The present invention includes pharmaceutical compositions comprising a substantially pure compound of the invention, or a pharmaceutically acceptable salt, stereoisomer, or hydrate thereof, and a pharmaceutically acceptable excipient and/or diluents.

The present invention also includes methods of treating erectile dysfunction, comprising administering to a human or animal an effective amount of compounds of the invention.

DETAILED DESCRIPTION

The compounds of the invention provide improved pharmacokinetic properties over the prior 2-phenyl substituted imidazoloatriazinone compounds by modifying the non-specific in vivo protein binding of the compounds. The pharmacokinetically improved compounds of the invention preferably allow a minimum effective amount of the compound to be administered to achieve the desired therapeutic effect of the unbound compound, thereby reducing the dosage amount (and may improve patient compliance).

In one embodiment, the present invention provides a compound of the formula A:

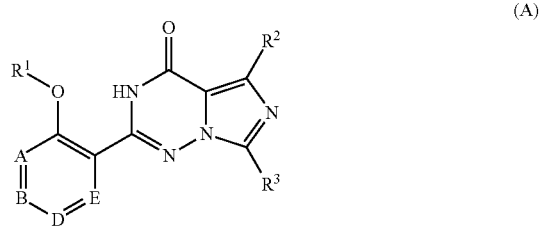

(A)

or pharmaceutically acceptable salt, stereoisomer, or hydrate thereof, wherein $R^1$ is lower alkyl;

$R^2$ is selected from lower alkyl, lower alkenyl and lower alkynyl, wherein the lower alkyl, lower alkenyl, and lower alkynyl may be optionally substituted with one or more halogen, lower alkoxy, hydroxy, CN, $NO_2$, amino, acylamino, amido, carbonyl, and alkylthio;

$R^3$ is selected from lower alkyl, lower alkenyl and lower alkynyl, wherein the lower alkyl, lower alkenyl, and lower alkynyl may be optionally substituted with one or more halogen, lower alkoxy, hydroxy, CN, $NO_2$, amino, acylamino, amido, carbonyl, and alkylthio;

A is N or C—H;

B is N, C—H, C—($SO_2$—$R^4$), or C—CO—$R^4$;

D is N, C—H, C—($SO_2$—$R^4$) or C—CO—$R^4$;

E is N or C—H;

wherein only one of A, B or E may be N, and one of B or D is C—($SO_2$—$R^4$) or C—CO—$R^4$;

$R^4$ is a group having the formula:
—NH—$R^{41}$,
—N($R^{42}$)($R^{43}$),

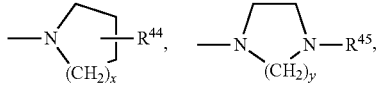

and
—N($R^{46}$)$_2$;

$R^{41}$ is selected from $C_3$-$C_6$ alkyl, $C_2$-$C_3$alkyl-OH, —($CH_2$), N(H)($R^{51}$) and —($CH_2$)$_a$—N($R^{52}$)($R^{53}$);

$R^{51}$ is selected from alkyl, cycloalkyl, cycloalkenyl, alkyl-O-alkyl, alkenyl, alkynyl, aralkyl, aryl and a heterocyclic group;

$R^{52}$ and $R^{53}$ are taken together with the nitrogen to which they are attached to form a 5- to 7-membered ring which is substituted at a ring carbon with one or two oxo groups and which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group, a is 1 to 6;

$R^{42}$ is selected from alkyl, and $C_2$-$C_6$alkyl-O-alkyl;

$R^{43}$ is selected from alkyl, $C_2$-$C_6$alkyl-NH-alkyl, $C_2$-$C_6$alkyl-O-alkyl, alkyl-$CO_2$H, $C_2$-$C_6$alkyl-CH(O-alkyl)(O-alkyl), $C_2$-$C_6$alkyl-$CH_2$(O-alkyl)-alkyl-O-alkyl, —($CH_2$)$_a$—N(H)($R^{51}$) and —($CH_2$)$_a$—N($R^{52}$)($R^{53}$);

$R^{44}$ is selected from is selected from the group consisting of
—($CH_2$)$_q$—N($R^{12}$)($R^{13}$), —($CH_2$)$_r$—N($R^{11}$)—($CH_2$)$_s$C(O)$R^{14}$, —($CH_2$)$_q$—C(O)$R^{14}$,
—($CH_2$)$_r$—C(O)—($CH_2$)$_s$O$R^{11}$, —($CH_2$)$_r$—C(O)—($CH_2$)$_s$N($R^{12}$)($R^{13}$), and
—($CH_2$)$_r$O—($CH_2$)$_s$—C(O)$R^{14}$, each $R^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

q is 1 to 6:

r is 0 to 6;

s is 0 to 6;

$R^{45}$ is selected from is selected from the group consisting of
—($CH_2$)$_v$—N($R^{25}$)($R^{26}$), —($CH_2$)$_v$—N($R^{21}$)—($CH_2$)$_w$—C(O)$R^{24}$, —($CH_2$)$_v$—C(O)$R^{24}$,
—($CH_2$)$_t$—C(O)—($CH_2$)$_w$O$R^{21}$, —($CH_2$)$_t$—C(O)($CH_2$)$_w$—N($R^{22}$)($R^{23}$),
—($CH_2$)$_v$—O—($CH_2$)$_w$—C(O)$R^{24}$;

each $R^{21}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group, each $R^{24}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

$R^{25}$ and $R^{26}$ taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

t is 0 to 6;

v is 1 to 6;

w is 0 to 6;

x is 1 or 2;

y is 1 or 2; and $R^{46}$ are both selected from $C_2$-$C_6$alkyl-OH, and $C_2$-$C_6$alkyl-O—$C_2$-$C_6$alkyl.

In a preferred embodiment of the present invention, there is provided a compound of the formula $A^1$

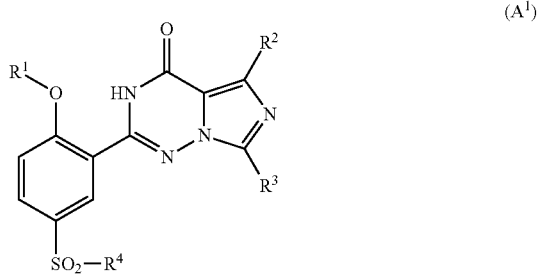

(A¹)

or pharmaceutically acceptable salt, stereoisomer, or hydrate thereof, wherein $R^1$ is lower alkyl;

$R^2$ and $R^3$ are independently selected from lower alkyl, and lower alkenyl and lower alkynyl, wherein the lower alkyl, lower alkenyl, and lower alkynyl may be optionally substituted with one or more halogen, lower alkoxy, hydroxy, CN, $NO_2$, amino, acylamino, amido, carbonyl, and alkylthio;

$R^4$ is a group having the formula:
—NH—$R^{41}$,
—N($R^{42}$)($R^{43}$), $$-N\underset{(CH_2)_x}{\overset{}{\diagdown\diagup}}R^{44}, \quad -N\underset{(CH_2)_y}{\overset{}{\diagdown\diagup}}N-R^{45},$$

and
—N($R^{46}$)$_2$;

$R^{41}$ is selected from $C_3$-$C_6$ alkyl, $C_2$-$C_3$alkyl-OH, —($CH_2$)$_a$—N($R^{51}$) and —($CH_2$)$_a$—N($R^{52}$)($R^{53}$);

$R^{51}$ is selected from alkyl, cycloalkyl, cycloalkenyl, alkyl-O-alkyl, alkyl-O-aryl, alkenyl, alkynyl, aralkyl, aryl and a heterocyclic group;

$R^{52}$ and $R^{53}$ are taken together with the nitrogen to which they are attached to form a 5- to 7-membered ring which is substituted at a ring carbon with one or two oxo groups and which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group, a is 1 to 6;

$R^{42}$ is selected from alkyl, and $C_2$-$C_6$alkyl-O-alkyl;

$R^{43}$ is selected from alkyl, $C_2$-$C_6$alkyl-NH-alkyl, $C_2$-$C_6$alkyl-O-alkyl, alkyl-$CO_2$H, $C_2$-$C_6$alkyl-CH(O-alkyl)(O-alkyl), $C_2$-$C_6$alkyl-$CH_2$(O-alkyl)-alkyl-O-alkyl, —($CH_2$)$_a$—N(H)($R^{51}$) and —($CH_2$)$_a$—N($R^{52}$)($R^{53}$);

$R^{44}$ is selected from is selected from the group consisting of
—($CH_2$)$_q$—N($R^{12}$)($R^{13}$), —($CH_2$)$_r$—N($R^{11}$)—($CH_2$)$_s$C(O)$R^{14}$, —($CH_2$)$_q$C(O)$R^{14}$,
—($CH_2$)$_r$—C(O)—($CH_2$)$_s$O$R^{11}$, —($CH_2$)$_r$C(O)—($CH_2$)$_s$N($R^{12}$)($R^{13}$), and
—($CH_2$)$_r$O—($CH_2$)$_s$—C(O)$R^{14}$, each $R^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

q is 1 to 6:
r is 0 to 6;
s is 0 to 6;

$R^{45}$ is selected from is selected from the group consisting of
—($CH_2$)$_v$—N($R^{25}$)($R^{26}$), ($CH_2$)$_v$—N($R^{21}$)—($CH_2$)$_w$—C(O)$R^{24}$, —($CH_2$)$_v$—C(O)$R^{24}$,
—($CH_2$)$_t$—C(O)—($CH_2$)$_w$O$R^{21}$, —($CH_2$)$_t$—C(O)($CH_2$)$_w$—N($R^{22}$)($R^{23}$),
—($CH_2$)$_v$—O—($CH_2$)$_w$—C(O)$R^{24}$;

each $R^{21}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group, each $R^{24}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

$R^{25}$ and $R^{26}$ taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

t is 0 to 6;
v is 1 to 6;
w is 0 to 6;
x is 1 or 2;
y is 1 or 2; and $R^{46}$ are both selected from $C_2$-$C_6$alkyl-OH, and $C_2$-$C_6$alkyl-O—$C_2$-$C_6$alkyl.

In another preferred embodiment of the present invention, there is provided a compound of the formula B:

(A$_2$)

or pharmaceutically acceptable salt, stereoisomer, or hydrate thereof, wherein $R^4$ is a group having the formula:
—NH—$R^{41}$,
—N($R^{42}$)($R^{43}$);

$$-N\underset{(CH_2)_x}{\overset{}{\diagdown\diagup}}R^{44}, \quad -N\underset{(CH_2)_y}{\overset{}{\diagdown\diagup}}N-R^{45},$$

and
—N($R^{46}$)$_2$;

$R^{41}$ is selected from $C_3$-$C_6$ alkyl, $C_2$-$C_3$alkyl-OH, —($CH_2$), N(H)($R^{51}$) and —($CH_2$)$_a$—N($R^{52}$)($R^{53}$);

$R^{51}$ is selected from alkyl, cycloalkyl, cycloalkenyl, alkyl-O-aryl, alkenyl, alkynyl, aralkyl, aryl and a heterocyclic group;

$R^{52}$ and $R^{53}$ are taken together with the nitrogen to which they are attached to form a 5- to 7-membered ring which is substituted at a ring carbon with one or two oxo groups and which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group, a is 1 to 6;

$R^{42}$ is selected from alkyl, and $C_2$-$C_6$alkyl-O-alkyl;

R⁴³ is selected from alkyl, C₂-C₆alkyl-NH-alkyl, C₂-C₆alkyl-O-alkyl, alkyl-CO₂H, C₂-C₆alkyl-CH(O-alkyl)(O-alkyl), C₂-C₆alkyl-CH₂(O-alkyl)-alkyl-O-alkyl, —(CH₂)ₙ—N(H)(R⁵¹) and —(CH₂)ₙ—N(R⁵²)(R⁵³);

R⁴⁴ is selected from is selected from the group consisting of —(CH₂)_q—N(R¹²)(R¹³), —(CH₂)_r—N(R¹¹)—(CH₂)_sC(O)R¹⁴, —(CH₂)_q—C(O)R¹⁴, —(CH₂)_r—C(O)—(CH₂)₃OR¹¹, —(CH₂)_r—C(O)—(CH₂)_sN(R¹²)(R¹³), and —(CH₂)_r,O—(CH₂)_s—C(O)R¹⁴, each R¹¹ is independently selected from H, alkyl, alkyl-O-alkyl, alkyl-O-aryl, alkenyl, alkynyl, cycloalkyl, cycloalkenyl, aralkyl, aryl and a heterocyclic group;

each R¹² and R¹³ are independently selected from H, alkyl, cycloalkyl, cycloalkenyl, alkyl-O-alkyl, alkyl-O-aryl, alkenyl, alkynyl, aralkyl, aryl and a heterocyclic group; or R¹² and R¹³ may be taken together with the nitrogen to which they are attached form a 5- to 7-membered ring which may optionally contain a further heteroatom and may be optionally substituted with up to three substituents selected from halo, CN, NO₂, oxo, alkyl, cycloalkyl, alkenyl, alkynyl, aralkyl, aryl, and a heterocyclic group;

each R¹⁴ is independently selected from H, alkyl, —OH, —O-alkyl, —O-aryl, —O-alalkyl, alkyl-O-alkyl, -alkyl-O-aryl, alkenyl, alkynyl, cycloalkyl, cycloalkenyl, aralkyl, aryl and a heterocyclic group;

q is 1 to 6:
r is 0 to 6;
s is 0 to 6;

R⁴⁵ is selected from is selected from the group consisting of —(CH₂)_v—N(R²⁵)(R²⁶), —(CH₂)_v—N(R²¹)—(CH₂)_w—C(O)R²⁴, —(CH₂)_v—C(O)R²⁴, —(CH₂)_t—C(O)—(CH₂)_wOR²¹, —(CH₂)_t—C(O)(CH₂)_w—N(R²²)(R²³), —(CH₂)_v—O—(CH₂)_w—C(O)R²⁴;

each R²¹ is independently selected from H, alkyl, alkyl-O-alkyl, alkyl-O-aryl, alkenyl, alkynyl, cycloalkyl, cycloalkenyl, aralkyl, aryl and a heterocyclic group;

each R²² and R²³ are independently selected from H, alkyl, cycloalkyl, cycloalkenyl, alkyl-O-alkyl, alkyl-O-aryl, alkenyl, alkynyl, aralkyl, aryl and a heterocyclic group; or R²² and R²³ may be taken together with the nitrogen to which they are attached form a 5- to 7-membered ring which may optionally contain a further heteroatom and may be optionally substituted with up to three substituents selected from halo, CN, NO₂, oxo, alkyl, cycloalkyl, alkenyl, alkynyl, aralkyl, aryl, and a heterocyclic group, each R²⁴ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

R²⁵ and R²⁶ taken together with the nitrogen to which they are attached form a 5- to 7-membered ring which may optionally contain a further heteroatom and may be optionally substituted with up to three substituents selected from halo, CN, NO₂, oxo, alkyl, cycloalkyl, alkenyl, alkynyl, aralkyl, aryl, and a heterocyclic group;

t is 0 to 6;
v is 1 to 6;
w is 0 to 6;
x is 1 or 2;
y is 1 or 2; and
R⁴⁶ are both selected from C₂-C₆alkyl-OH, and C₂-C₆alkyl-O—C₂-C₆alkyl.

In another preferred embodiment of the present invention, there is provided a compound having the formula:

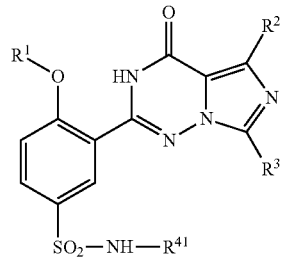

(B₁)

wherein,
or pharmaceutically acceptable salt, stereoisomer, or hydrate thereof, wherein R¹ is lower alkyl;

R² and R³ are independently selected from lower alkyl, and lower alkenyl and lower alkynyl, wherein the lower alkyl, lower alkenyl, and lower alkynyl may be optionally substituted with one or more halogen, lower alkoxy, hydroxy, CN, NO₂, amino, acylamino, amido, carbonyl, and alkylthio;

R⁴¹ is selected from C₃-C₆ alkyl, C₂-C₃alkyl-OH, —(CH₂)_a—N(H)(R⁵¹) and —(CH₂)_a—N(R⁵²)(R⁵³);

R⁵¹ is selected from alkyl, cycloalkyl, cycloalkenyl, alkyl-O-alkyl, alkyl-O-aryl, alkenyl, alkynyl, aralkyl, aryl and a heterocyclic group;

R⁵² and R⁵³ are taken together with the nitrogen to which they are attached to form a 5- to 7-membered ring which is substituted at a ring carbon with one or two oxo groups and which may optionally contain a further heteroatom and may be optionally substituted with up to three substituents selected from halo, CN, NO₂, oxo, alkyl, cycloalkyl, alkenyl, alkynyl, aralkyl, aryl, and a heterocyclic group, a is 1 to 6;

R²² and R²³ are independently selected from H, alkyl, cycloalkyl, cycloalkenyl, alkyl-O-alkyl, alkyl-O-aryl, alkenyl, alkynyl, aralkyl, aryl and a heterocyclic group; or R²² and R²³ may be taken together with the nitrogen to which they are attached form a 5- to 7-membered ring which may optionally contain a further heteroatom and may be optionally substituted with up to three substituents selected from halo, CN, NO₂, oxo, alkyl, cycloalkyl, alkenyl, alkynyl, aralkyl, aryl, and a heterocyclic group; and v is 1 to 6.

In another preferred embodiment of the present invention, there is provided a compound having the formula:

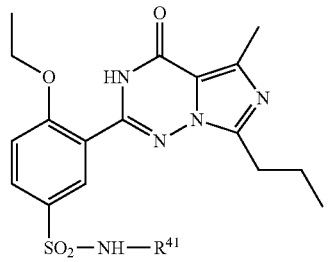

(B₂)

wherein,
R⁴¹ is selected from C₃-C₆ alkyl, C₂-C₃alkyl-OH, —(CH₂)_a—N(H)(R⁵¹) and —(CH₂)_a—N(R⁵²)(R⁵³);

R⁵¹ is selected from alkyl, cycloalkyl, cycloalkenyl, alkyl-O-alkyl, alkyl-O-aryl, alkenyl, alkynyl, aralkyl, aryl and a heterocyclic group;

R⁵² and R⁵³ are taken together with the nitrogen to which they are attached to form a 5- to 7-membered ring which is substituted at a ring carbon with one or two oxo groups and which may optionally contain a further heteroatom and may be optionally substituted with up to three substituents selected from halo, CN, NO₂, oxo, alkyl, cycloalkyl, alkenyl, alkynyl, aralkyl, aryl, and a heterocyclic group, a is 1 to 6;

$R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group;

or $R^{22}$ and $R^{23}$ may be taken together with the nitrogen to which they are attached form a 5- to 7-membered ring which may optionally contain a further heteroatom and may be optionally substituted with up to three substituents selected from halo, CN, NO₂, oxo, alkyl, cycloalkyl, alkenyl, alkynyl, aralkyl, aryl, and a heterocyclic group; and v is 1 to 6.

Representative compounds of the formula B₂ are provided below:

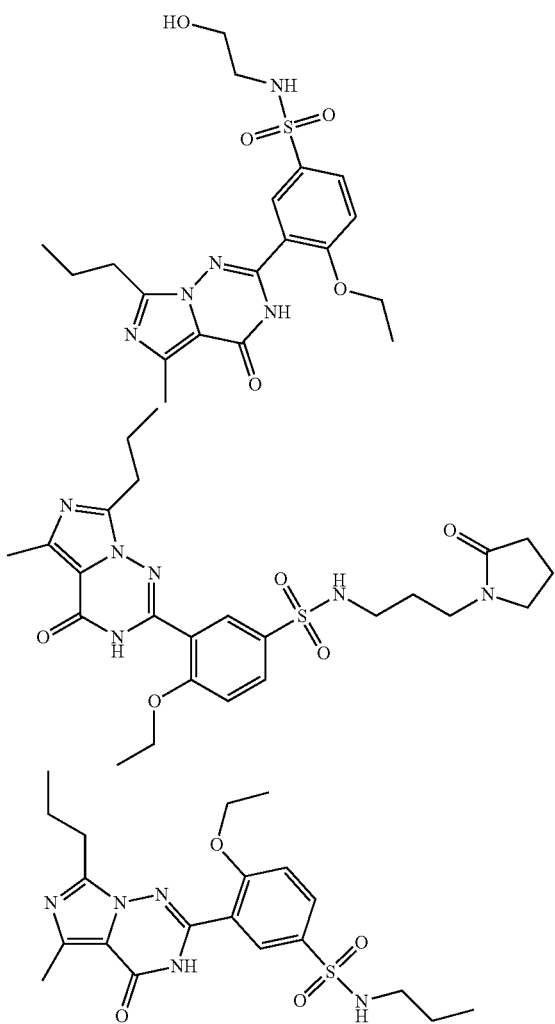

In another preferred embodiment of the present invention, there is provided a compound having the formula:

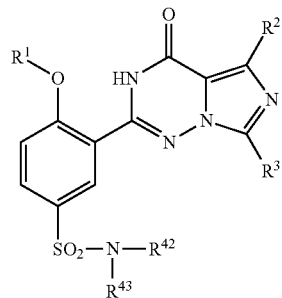

(C₁)

or pharmaceutically acceptable salt, stereoisomer, or hydrate thereof, wherein $R^1$ is lower alkyl;

$R^2$ and $R^3$ are independently selected from lower alkyl, and lower alkenyl and lower alkynyl, wherein the lower alkyl, lower alkenyl, and lower alkynyl may be optionally substituted with one or more halogen, lower alkoxy, hydroxy, CN, NO₂, amino, acylamino, amido, carbonyl, and alkylthio;

$R^{42}$ is selected from alkyl, and $C_2$-$C_6$alkyl-O-alkyl;

$R^{43}$ is selected from alkyl, $C_2$-$C_6$alkyl-NH-alkyl, $C_2$-$C_6$alkyl-O-alkyl, alkyl-CO₂H, $C_2$-$C_6$alkyl-CH(O-alkyl)(O-alkyl), $C_2$-$C_6$alkyl-CH₂(O-alkyl)-alkyl-O-alkyl, —(CH₂)$_a$—N(H)($R^{51}$) and —(CH₂)$_a$—N($R^{52}$)($R^{53}$);

$R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group;

or $R^{22}$ and $R^{23}$ may be taken together with the nitrogen to which they are attached form a 5- to 7-membered ring which may optionally contain a further heteroatom and may be optionally substituted with up to three substituents selected from halo, CN, NO₂, oxo, alkyl, cycloalkyl, alkenyl, alkynyl, aralkyl, aryl, and a heterocyclic group; and v is 1 to 6.

In another preferred embodiment of the present invention, there is provided a compound having the formula:

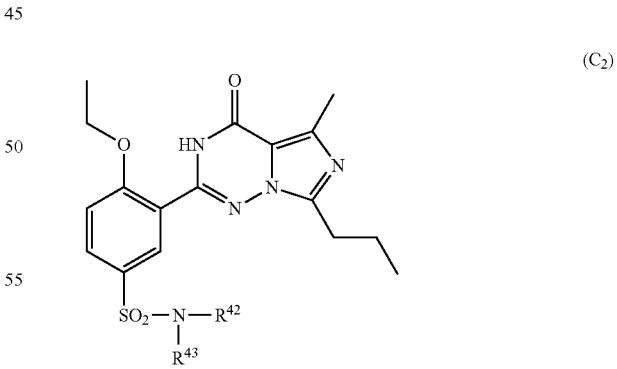

(C₂)

or pharmaceutically acceptable salt, stereoisomer, or hydrate thereof, wherein $R^{42}$ is selected from alkyl, and $C_2$-$C_6$alkyl-O-alkyl;

$R^{43}$ is selected from alkyl, $C_2$-$C_6$alkyl-NH-alkyl, $C_2$-$C_6$alkyl-O-alkyl, alkyl-CO₂H, $C_2$-$C_6$alkyl-CH(O-alkyl)(O-alkyl), $C_2$-$C_6$alkyl-CH₂(O-alkyl)-alkyl-O-alkyl, —(CH₂), N(H)($R^{51}$) and —(CH₂)$_a$—N($R^{52}$)($R^{53}$);

$R^{22}$ and a $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group;

or $R^{22}$ and $R^{23}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group; and v is 1 to 6.

Representative compounds of the formula $C_2$ are provided below:

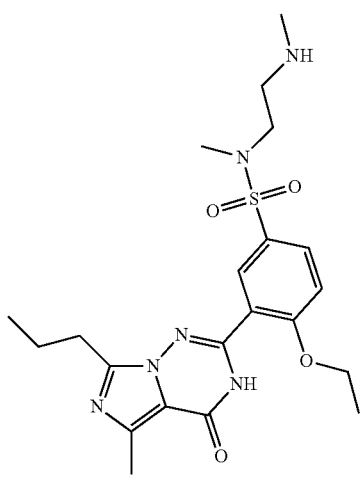

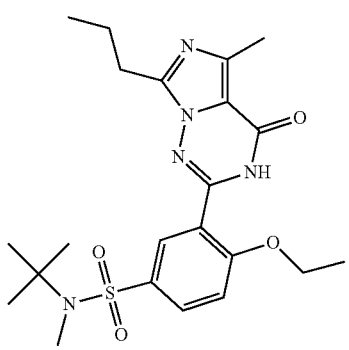

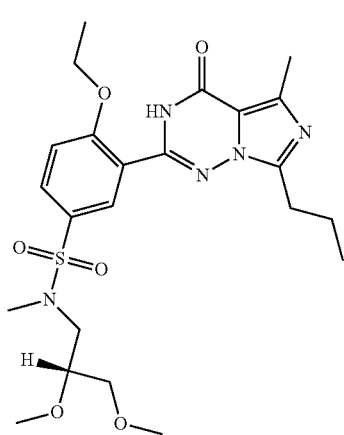

-continued

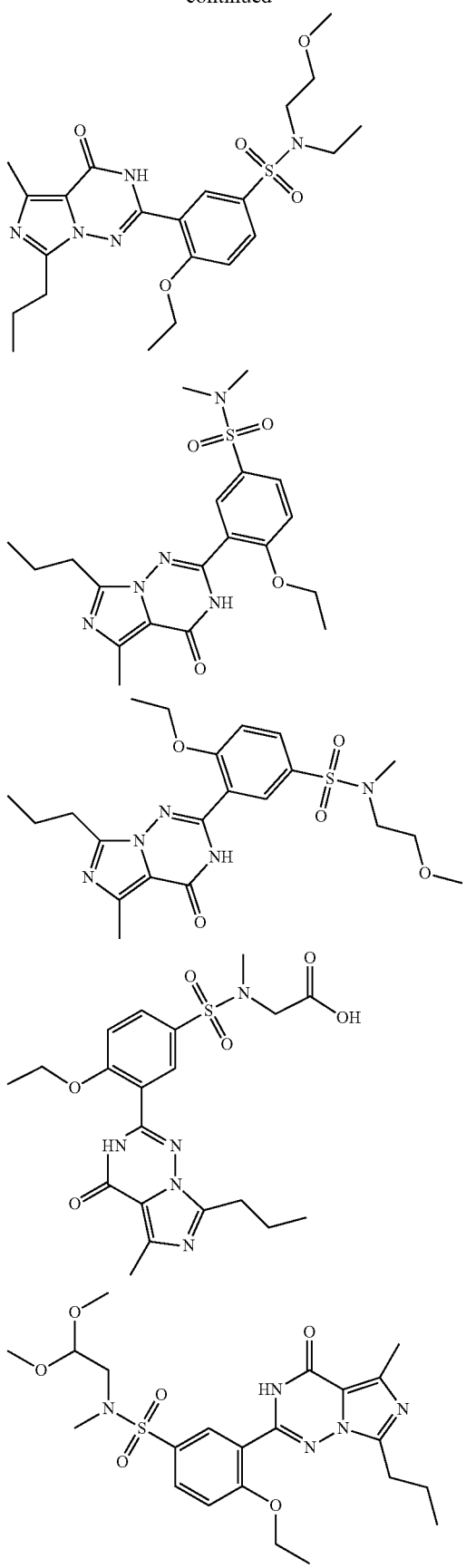

-continued

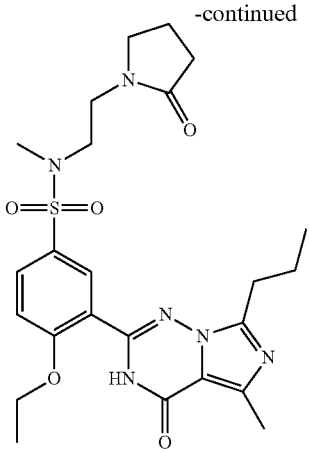

In another preferred embodiment of the present invention, there is provided a compound having the formula:

(D₁)

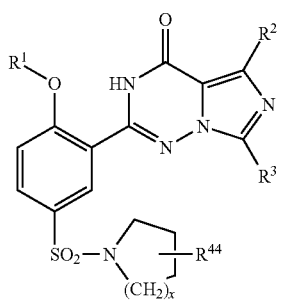

or pharmaceutically acceptable salt, stereoisomer, or hydrate thereof, wherein $R^1$ is lower alkyl;

$R^2$ and $R^3$ are independently selected from lower alkyl, and lower alkenyl and lower alkynyl, wherein the lower alkyl, lower alkenyl, and lower alkynyl may be optionally substituted with one or more halogen, lower alkoxy, hydroxy, CN, $NO_2$, amino, acylamino, amido, carbonyl, and alkylthio;

$R^{44}$ is selected from is selected from the group consisting of
—$(CH_2)_q$—$N(R^{12})(R^{13})$, —$(CH_2)_r$—$N(R^{11})$—$(CH_2)_s$C(O)$R^{14}$, —$(CH_2)_q$—$C(O)R^{14}$,
—$(CH_2)_r$—$C(O)$—$(CH_2)_s$$OR^{11}$, —$(CH_2)_r$—$C(O)$—$(CH_2)_s$$N(R^{12})(R^{13})$, and
—$(CH_2)_r$O—$(CH_2)_s$C(O)$R^{14}$, each $R^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

q is 1 to 6:

r is 0 to 6;

s is 0 to 6; and x is 1 or 2.

In another preferred embodiment of the present invention, there is provided a compound having the formula:

(D₂)

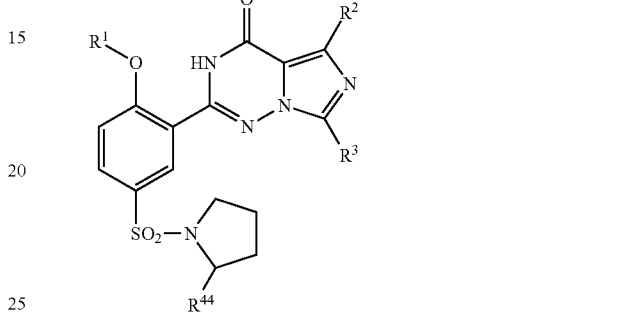

or pharmaceutically acceptable salt, stereoisomer, or hydrate thereof, wherein $R^1$ is lower alkyl;

$R^2$ and $R^3$ are independently selected from lower alkyl, and lower alkenyl and lower alkynyl, wherein the lower alkyl, lower alkenyl, and lower alkynyl may be optionally substituted with one or more halogen, lower alkoxy, hydroxy, CN, $NO_2$, amino, acylamino, amido, carbonyl, and alkylthio;

$R^{44}$ is selected from is selected from the group consisting of
—$(CH_2)_q$—$N(R^{12})(R^{13})$, —$(CH_2)_r$—$N(R^{11})$—$(CH_2)_s$C(O)$R^{14}$, —$(CH_2)_q$—$C(O)R^{14}$,
—$(CH_2)_r$C(O)—$(CH_2)_s$$OR^{11}$, —$(CH_2)_r$—$C(O)$—$(CH_2)_s$$N(R^{12})(R^{13})$, and
—$(CH_2)_r$O—$(CH_2)_s$—$C(O)R^{14}$, each $R^{11}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{12}$ and $R^{13}$ are independently selected from H, alkyl, cycloalkyl, cycloalkenyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

each $R^{14}$ is independently selected from H, alkyl, —OH, —O-alkyl, —O-aryl, —O-aralkyl, -alkyl-O-aryl, alkenyl, alkynyl, cycloalkyl, cycloalkenyl, aralkyl, aryl and a heterocyclic group;

q is 1 to 6:

r is 0 to 6;

s is 0 to 6.

In another preferred embodiment of the present invention, there is provided a compound having the formula:

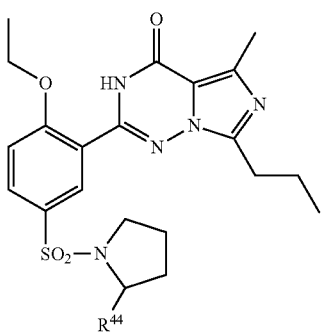

(D₃)

or pharmaceutically acceptable salt, stereoisomer, or hydrate thereof, wherein

R⁴⁴ is selected from is selected from the group consisting of
—(CH₂)$_q$—N(R¹²)(R¹³), —(CH₂)$_r$—N(R¹¹)—(CH₂)$_s$C(O)R¹⁴, —(CH₂)$_q$—C(O)R¹⁴,
—(CH₂)$_r$—C(O)—(CH₂)$_s$OR¹¹, —(CH₂)$_r$—C(O)—(CH₂)$_s$N(R¹²)(R¹³), and
—(CH₂)$_r$O—(CH₂)$_s$—C(O)R¹⁴, each R¹¹ is independently selected from H, alkyl, alkyl-O-alkyl, alkyl-O-aryl, alkenyl, alkynyl, cycloalkyl, cycloalkenyl, aralkyl, aryl and a heterocyclic group;

each R¹² and R¹³ are independently selected from H, alkyl, cycloalkyl, cycloalkenyl, alkyl-O-alkyl, alkyl-O-aryl, alkenyl, alkynyl, aralkyl, aryl and a heterocyclic group; or R¹² and R¹³ may be taken together with the nitrogen to which they are attached form a 5- to 7-membered ring which may optionally contain a further heteroatom and may be optionally substituted with up to three substituents selected from halo, CN, NO₂, oxo, alkyl, cycloalkyl, alkenyl, alkynyl, aralkyl, aryl, and a heterocyclic group;

each R¹⁴ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

q is 1 to 6:
r is 0 to 6;
s is 0 to 6.

A representative compound of the formula D₃ are provided below:

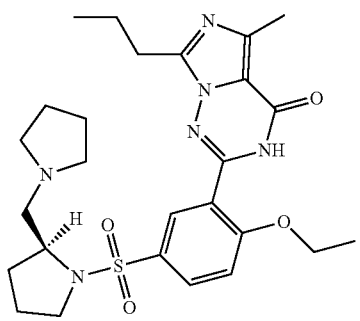 [SMILES: CCCc1nc(C)c2c(=O)[nH]c(-c3cc(S(=O)(=O)N4CCC[C@H]4CN4CCCC4)ccc3OCC)nn12]

In another preferred embodiment of the present invention, there is provided a compound having the formula:

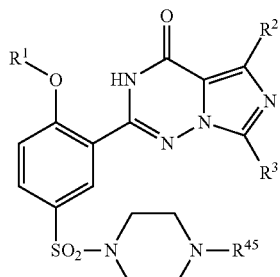

(E₁)

or pharmaceutically acceptable salt, stereoisomer, or hydrate thereof, wherein

R¹ is lower alkyl;

R² and R³ are independently selected from lower alkyl, and lower alkenyl and lower alkynyl, wherein the lower alkyl, lower alkenyl, and lower alkynyl may be optionally substituted with one or more halogen, lower alkoxy, hydroxy, CN, NO₂, amino, acylamino, amido, carbonyl, and alkylthio;

R⁴⁵ is selected from is selected from the group consisting of
—(CH₂)$_v$—N(R²⁵)(R²⁶), —(CH₂)$^v$—N(R²¹)—(CH₂)$_w$—C(O)R²⁴, —(CH₂)$_v$—C(O)R²⁴,
—(CH₂)$_t$—C(O)—(CH₂)$_w$OR²¹, —(CH₂)$_t$—C(O)(CH₂)$_w$—N(R²²)(R²³),
—(CH₂)$_v$—O—(CH₂)$_w$—C(O)R²⁴;

each R²¹ is independently selected from H, alkyl, alkyl-O-alkyl, alkyl-O-aryl, alkenyl, alkynyl, cycloalkyl, cycloalkenyl, aralkyl, aryl and a heterocyclic group;

each R²² and R²³ are independently selected from H, alkyl, cycloalkyl, cycloalkenyl, alkyl-O-alkyl, alkyl-O-aryl, alkenyl, alkynyl, aralkyl, aryl and a heterocyclic group; or R²² and R²³ may be taken together with the nitrogen to which they are attached form a 5- to 7-membered ring which may optionally contain a further heteroatom and may be optionally substituted with up to three substituents selected from halo, CN, NO₂, oxo, alkyl, cycloalkyl, alkenyl, alkynyl, aralkyl, aryl, and a heterocyclic group, each R²⁴ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

R²⁵ and R²⁶ taken together with the nitrogen to which they are attached form a 5- to 7-membered ring which may optionally contain a further heteroatom and may be optionally substituted with up to three substituents selected from halo, CN, NO₂, oxo, alkyl, cycloalkyl, alkenyl, alkynyl, aralkyl, aryl, and a heterocyclic group;

t is 0 to 6;
v is 1 to 6;
w is 0 to 6.

In another preferred embodiment of the present invention, there is provided a compound having the formula:

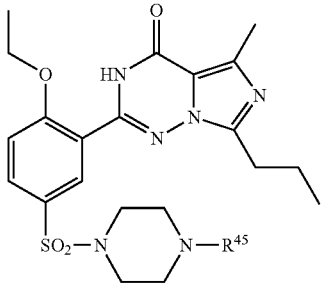
(E₂)

or pharmaceutically acceptable salt, stereoisomer, or hydrate thereof, wherein $R^{45}$ is selected from is selected from the group consisting of —$(CH_2)_v$—$N(R^{25})(R^{26})$, —$(CH_2)_v$—$N(R^{21})$—$(CH_2)_w$—$C(O)R^{24}$, —$(CH_2)_v$—$C(O)R^{24}$, —$(CH_2)_t$—$C(O)$—$(CH_2)_w OR^{21}$, —$(CH_2)_t$—$C(O)(CH_2)_w$—$N(R^{22})(R^{23})$, —$(CH_2)_v$—O—$(CH_2)_w$—$C(O)R^{24}$;

each $R^{21}$ is independently selected from H, alkyl, alkyl-O-alkyl, alkyl-O-aryl, alkenyl, alkynyl, cycloalkyl, cycloalkenyl, aralkyl, aryl and a heterocyclic group;

each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group, each $R^{24}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

$R^{25}$ and $R^{26}$ taken together with the nitrogen to which they are attached four a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

t is 0 to 6;

v is 1 to 6; and w is 0 to 6.

Representative compounds of the formula $E_2$ are provided below:

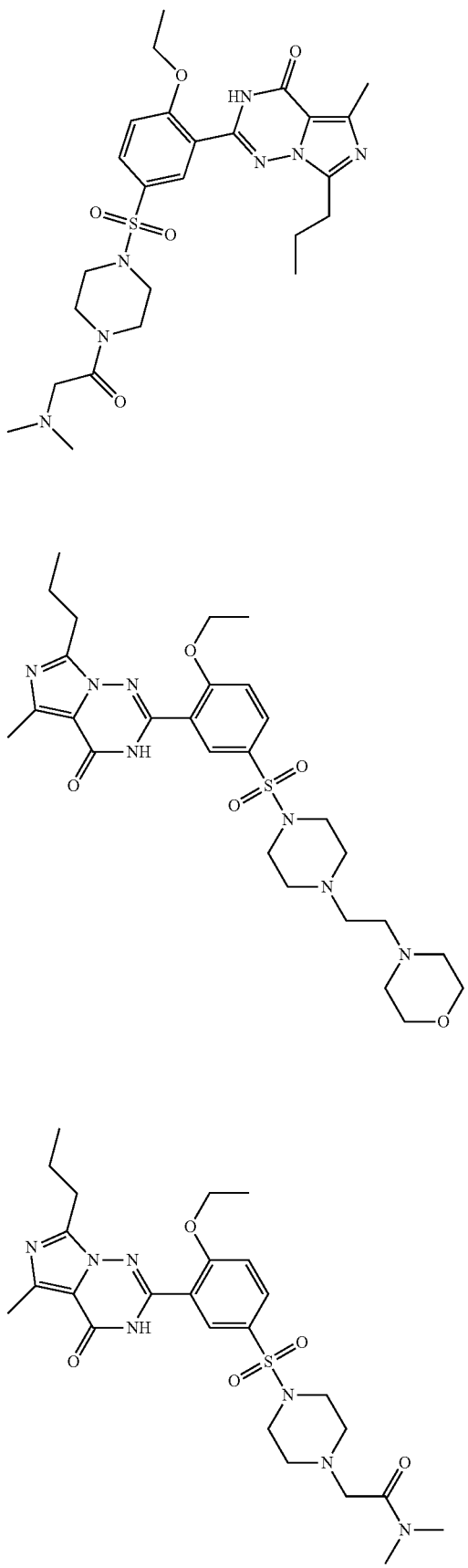

-continued

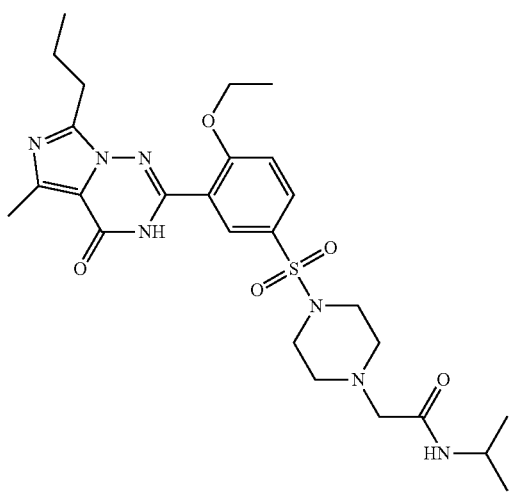

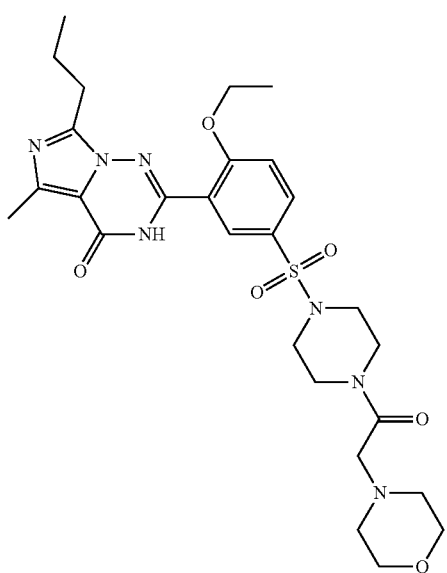

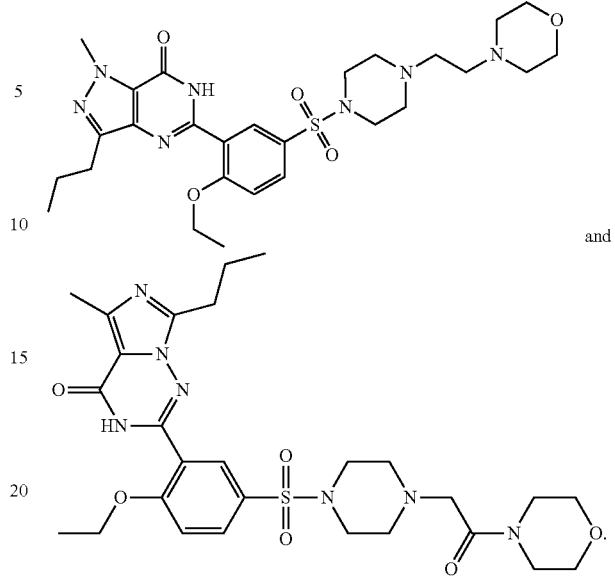

In another preferred embodiment of the present invention, there is provided a compound having the formula:

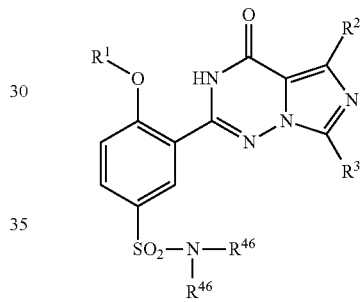

or pharmaceutically acceptable salt, stereoisomer, or hydrate thereof, wherein
$R^1$ is lower alkyl;
$R^2$ and $R^3$ are independently selected from lower alkyl, and lower alkenyl and lower alkynyl, wherein the lower alkyl, lower alkenyl, and lower alkynyl may be optionally substituted with one or more halogen, lower alkoxy, hydroxy, CN, $NO_2$, amino, acylamino, amido, carbonyl, and alkylthio;
$R^{46}$ are both selected from $C_2$-$C_6$alkyl-OH, and $C_2$-$C_6$alkyl-O—$C_2$-$C_6$alkyl.

In another preferred embodiment of the present invention, there is provided a compound having the formula:

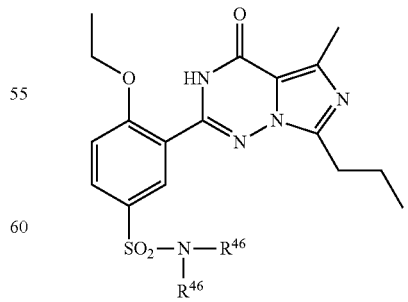

or pharmaceutically acceptable salt, stereoisomer, or hydrate thereof, wherein
$R^{46}$ are both selected from $C_2$-$C_6$alkyl-OH, and $C_2$-$C_6$alkyl-O—$C_2$-$C_6$alkyl.

It is believed that the substituent $R^4$ modulates the pharmacokinetic and/or pharmacodynamic profile of the compound and may result in improved pharmacokinetic properties compared to the unmodified, i.e. parent compound. In certain embodiments, the active agent has improved physicochemical properties, pharmacokinetics, metabolism, or toxicity profile. In a preferred embodiment, the active agent has superior solubility, lower $IC_{50}$, and/or is substantially less protein bound in vivo compared to the compound lacking the at least one functional residue.

Preferably, the compounds of the invention include but are not limited to inhibitors and activators of proteins and enzymes (e.g., phosphodiesterases such as PDE5, PDE1, PDE3 and PDE6, kinases, growth factor receptors, and proteases).

The term "heteroatom" as used herein means an atom of any element other than carbon or hydrogen. Preferred heteroatoms are boron, nitrogen, oxygen, phosphorus, sulfur and selenium. Most preferred are nitrogen or oxygen.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups each having up to 20 carbon atoms. In preferred embodiments, a straight chain or branched chain alkyl has 10 or fewer carbon atoms in its backbone (e.g., $C_1$-$C_{10}$ for straight chain, $C_3$-$C_{10}$ for branched chain), and more preferably 6 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to six carbons, and more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5- and 6-membered single-ring aromatic groups that may include from zero to four heteroatoms, for example, benzene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, aryls and/or heterocyclic groups.

The terms "heterocyclyl" or "heterocyclic group" refer to 3- to 10-membered ring structures, more preferably 5- or 6-membered rings, whose ring structures include one to four heteroatoms. Heterocycles can also be polycycles. Heterocyclic groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, aryls and/or heterocyclyls) in which two or more carbons are common to two adjoining rings, e.g., the rings are "fused rings". Rings that are joined through non-adjacent atoms are termed "bridged" rings. Each of the rings of the polycyclic group can be substituted with such substituents as described above, for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

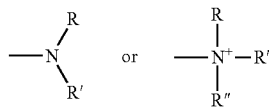

wherein R, R' and R" each independently represent a group permitted by the rules of valence, preferably H, alkyl, alkenyl, alkynyl, aralkyl, aryl, and heterocyclic groups.

The term "acylamino" is art-recognized and refers to a moiety that can be represented by the general formula:

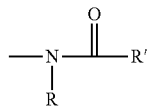

wherein R and R' are as defined above.

The term "amido" is art recognized as an amino-substituted carbonyl and includes a moiety that can be represented by the general formula:

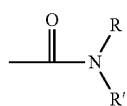

wherein R, R' are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R'$_8$, wherein m and R'$_8$ are defined above. Representative alkylthio groups include methylthio, ethyl thio, and the like.

The term "carbonyl" is art recognized and includes such moieties as can be represented by the general formula:

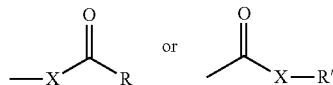

wherein X is a bond or represents an oxygen or a sulfur, and R and R' are as defined above.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like.

The term "sulfonate" is art recognized and includes a moiety that can be represented by the general formula:

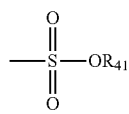

in which R$_{41}$ is an electron pair, hydrogen, alkyl, cycloalkyl, or aryl.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

The term "sulfate" is art recognized and includes a moiety that can be represented by the general formula:

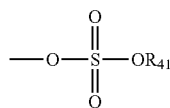

in which R$_{41}$ is as defined above.

The term "sulfonylamino" is art recognized and includes a moiety that can be represented by the general formula:

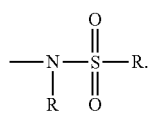

The term "sulfamoyl" is art-recognized and includes a moiety that can be represented by the general formula:

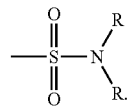

The term "sulfonyl", as used herein, refers to a moiety that can be represented by the general formula:

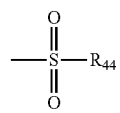

in which R$_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

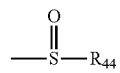

in which R$_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R$_7$, m and R$_7$ being defined above.

Analogous substitutions can be made to alkenyl and alkynyl groups to produce, for example, aminoalkenyls, aminoalkynyls, aminoalkenyls, aminoalkynyls, iminoalkenyls, iminoalkynyls, thioalkenyls, thioalkynyls, carbonyl-substituted alkenyls or alkynyls.

As used herein, the definition of each expression, e.g. alkyl, m, n, R, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Table 1-3 summarizes certain biological and pharmacological properties of the above-described modified compounds of A. Table 3 includes selectivity index against several PDEs. The protein binding, permeability, and solubility of the above-described compounds are set forth in Table 2.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are included in this invention.

In addition, if, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The compounds of the present invention may act as inhibitors of one or more phosphodiesterases, including, for example PDE1, PDE2 and PDE5. The compounds of the present invention can be employed in pharmaceuticals for maintenance or restoration of endothelial health and cardiovascular health and for treatment of conditions relating to the inhibition of phosphodiesterases, particularly PDE5. For example, the compounds of the invention may be used for the treatment of cardiovascular disorders, including but not limited to hypertension, cerebrovascular disorders, and disorders of the urogenital system, particularly erectile dysfunction. Thus, the present invention also includes methods of treating cardiovascular disorders, hypertension, isolated systolic hypertension (ISH), pulmonary hypertension, acute heart failure, chronic heart failure, ischemic heart disease (including, but not limited to chronic angina), peripheral arterial disease, pre-eclampsia, Raynaud's Disease, endothelial dysfunction/pre-hypertension, chronic obstructive pulmonary disease (COPD), Meniere's disease, neuropathic pain in diabetes, cerebrovascular disorders, disorders of the urogenital system, benign prostatic hypertrophy, erectile dysfunction, and female sexual dysfunction comprising administering to a human or animal an effective amount of any of the above compounds.

For purposes of this invention, the chemical elements are identified in accordance with the Periodic Table of the Elements, CAS version, Handbook of Chemistry and Physics, 67th Ed., 1986-87, inside cover.

The compounds of the present invention which have been modified by the attachment thereto of at least one residue of the formula C provide modified pharmacokinetic properties, including modified nonspecific in vivo protein binding. Such optimal pharmacokinetic properties do not compromise either the selectivity or the potency of the modified compound.

The modification of protein binding is based on surface technology, i.e. the preparation and screening of surfaces for their ability to resist adsorption of proteins from solution. Surfaces which are resistant to adsorption of proteins from solution are known to one of skill in the art as "protein resistant" surfaces. Functional groups may be screened to identify the group(s) present in protein resistant surfaces, as described in e.g., Chapman et al. Surveying for Surfaces that Resist the Adsorption of Proteins, J. Am. Chem. Soc. 2000, 122:8303-8304; Ostuni et al. A Survey of Structure-Property Relationships of Surfaces that Resist the Adsorption of Protein, Langmuir 2001, 17:5605-5620; Holmlin, et al. Zwitterionic SAMs that Resist Nonspecific Adsorption of Protein from Aqueous Buffer, Langmuir 2001, 17:2841-2850; and Ostuni et al. Self-Assembled Monolayers that Resist the Adsorption of Proteins and the Adhesion of Bacterial and Mammalian Cells, Langmuir 2001, 17:6336-6343.

In general, protein binding is assessed by measuring the capacity of molecules of the invention to bind to one or more human serum components or mimics thereof. In one embodiment, suitable functional residues may be identified by screening of surfaces comprising such residues for their ability to resist adsorption of serum components, including, but not limited to serum proteins, and preferably human serum proteins. Candidate residues can be screened directly by attaching them to a solid support and testing the support for protein resistance. Alternatively, candidate residues are incorporated into, or linked to molecules of pharmaceutical interest. Such compounds may be synthesized on a solid support, or bound to a solid support after synthesis. In a non-limiting example of a direct binding assay, immobilized candidate functional residues or molecules incorporating such residues are tested for their ability to bind serum components. The serum components can be labeled with a signaling moiety for detection, or a labeled secondary reagent that binds to such serum components can be used.

Surfaces which are resistant to adsorption of proteins from solution are known as "protein resistant" surfaces. Functional groups may be screened to identify the group(s) present in protein resistant surfaces, as described in e.g., Chapman et al. Surveying for Surfaces that Resist the Adsorption of Proteins, J. Am. Chem. Soc. 2000, 122:8303-8304; Ostuni et al. A Survey of Structure-Property Relationships of Surfaces that Resist the Adsorption of Protein, Langmuir 2001, 17:5605-5620; Holmlin, et al. Zwitterionic SAMs that Resist Nonspecific Adsorption of Protein from Aqueous Buffer, Langmuir 2001, 17:2841-2850; and Ostuni et al. Self-Assembled Monolayers that Resist the Adsorption of Proteins and the Adhesion of Bacterial and Mammalian Cells, Langmuir 2001, 17:6336-6343.

Upon identification of a functional residue which provides such protein resistance, one of skill in the art will readily determine a suitable chemical skeleton or backbone of a known biologically or chemically active compound to which the functional residue may be attached by either substitution of functional group of the active compound or by replacement of a nonessential functional group of the active compound. For example, as discussed above, the presence of a piperazine group on a compound will indicate that such group may be either replaced or substituted with an functional residue. One of skill in the art, e.g. a medicinal chemist, will recognize other suitable groups on known active compounds which may be replaced or substituted with at least one functional residue.

Accordingly, a combinatorial library of compounds, may be generated as described infra, wherein the compounds are modified compounds comprising a conjugate of an active site of the compound (an essential backbone of a compound having a particular desired activity), e.g. compound A and at least one functional residue attached thereto, wherein each conjugate has a different functional residue attached thereto, e.g. residues having formula C, wherein each R group is selected from the various groups described herein. Accordingly, a library may be used to screen a plurality of different functional residues for improved pharmacokinetic and/or pharmacodynamic properties including non-specific protein binding of the modified compound.

In preferred embodiments, the solid support itself is chosen or modified to minimize its interaction with the serum components. Examples of such supports and assay systems are described in International Application WO 02/48676, WO 03/12392, WO 03/18854, WO 03/54515, herein incorporated by reference. Alternatively, the molecules of the invention may be mixed with one or more serum components in liquid phase, and the amount of unbound molecules determined.

A direct binding analysis can also be preformed in liquid phase. For example, test compounds can be mixed with one or more serum components in liquid phase, and the unbound molecules determined.

In an example of a preferred embodiment, molecules having reduced protein binding are identified as follows: a self-assembled monolayer of thiol molecules terminated with anhydride groups is formed at a gold surface. A set of small molecules with amine groups at one end, and groups that are designed to resist binding to albumin, for example, at the other end are then attached to the surface via reaction between the amine and anhydride. The set of molecules are spotted onto spatially distinct regions on the gold surface to create an array of molecules that might resist protein binding. This array is then exposed to a solution containing albumin that is fluorescently labeled. After a suitable incubation period, the gold surface is washed and scanned on a fluorescent scanner. The immobilized chemical groups that bound to albumin will be identified by the presence of a fluorescent signal; groups that resist albumin binding will have low fluorescence in that part of the array. If a fluorescent protein is not available then antibodies against the protein of interest in combination with fluorescent secondary antibodies can be used to detect protein binding to the chemical groups. If an antibody is not available then a labeless detection method such as surface plasmon resonance (SPR) or MALDI mass spectrometry can be used to identify the presence of the protein at individual elements in the array. SPR also has the advantage of providing kinetic information on the binding of protein to the chemical groups.

The use of this system is not limited to albumin; any protein of pharmacokinetic interest can be tested for binding potential. For example, blood proteins that bind small molecules, such as α-acid glycoprotein (AAG, AGP) and lipoproteins, could be exposed to the array and protein binding detected.

In an embodiment of the invention, chemical groups can be identified that resist binding to P-glycoprotein (PGP) and therefore have the potential to reduce efflux when appended to a small molecule therapeutic. This is particularly important for development of anti-cancer drugs provide effective treatment where multiple drug resistance (MDR) has developed.

The method could also be used to identify chemical groups that resist binding to proteins such as thrombin, anti-thrombin, and Factor Xa and therefore have the potential to control coagulation.

This method would also be useful for identifying groups that improve therapeutics that are designed as supplemental or replacement therapies where protein binding and PK properties are very important, e.g., hormones and their binding proteins, and steroids and their binding proteins such as testosterone and sex hormone binding globulin (SHBG).

The following describes a surface-based method for identifying groups that can improve the solubility of small molecules. A self-assembled monolayer of thiol molecules terminated with maleimide groups is formed at a gold surface. A set of small molecules with thiol groups at one end, and groups that are hydrophilic at the other end are then attached to the surface via reaction between the thiol and maleimide. The set of molecules are spotted onto spatially distinct regions on the gold surface to create an array of molecules that might increase the solubility of a small molecule. Droplets of both polar (e.g., water) and hydrophobic (e.g., octanol) liquids are then placed onto each element of the array. The contact angles of the two liquids on each element are then measured at each element of the array using a goniometer. Alternatively, the wettability of a particular liquid at a surface presenting a chemical group can be determined by measuring the area of the surface covered by a droplet when viewed from above (high contact angle will yield droplets of small area; low contact angles cover greater areas). The contact angle of a liquid on a surface presenting a chemical group is inversely proportional to the miscibility of that chemical group with that liquid (solvent). For example, a chemical group for which water has a high contact angle when it is presented at the surface, such as methyl ($CH_3$), has low miscibility with water, i.e., it will tend to reduce the solubility of a small molecule. Conversely, a chemical group for which water has a low contact angle when it is presented at the surface, such as carboxyl (COOH), has high miscibility with water, i.e., it will tend to increase the solubility of a small molecule. Sets of chemical groups can therefore be screened rapidly using contact angles on surfaces to identify groups that improve solubility or reduce hydrophilicity. This approach can be used to evaluate the effect on solubility of chemical groups used according to the invention.

A common parameter for the ability of a small molecule to cross the lipid membrane of a cell is log P where P is the partition coefficient of the compound between octanol and water. The relative contact angle of a surface presenting chemical groups for octanol and water therefore offers a rapid, empirical method for ranking large sets of chemical groups for their potential effect on the log P of a compound.

The pH dependence of the solubility of small molecules can be addressed in this method by measuring the contact angles of solutions at different pHs. The parameter equivalent to log P in this case is log D, where D is the distribution coefficient, defined as the ratio of the sum of the concentrations of all species of the compound in octanol to the sum of the concentrations of all species of the compound in water at various pHs. Contact angles measured at different pHs therefore offer the possibility of an equivalent measure to log D.

It will also be useful to screen candidate compounds for their capacity to be actively transported across cell membranes and cells, or for their resistance to such transport. For example, it is well known that pharmaceutically useful anti-cancer molecules may be limited in their effectiveness due to active transport out of target tumor cells. Similarly, monolayers of brain capillary endothelial cells have been observed to unidirectionally transport vincristine from basal side to apical side, effectively preventing the anti-cancer agent from entering the central nervous system. In some instances, chemical groups of value will, in addition to reducing non-specific protein binding, improve pharmcokinetics by enhancing passive or active transport towards their site of action, and/or inhibiting transport from the site of action.

The brain is one of the most difficult tissues for small molecules to penetrate. The neurovascular junctions are tight and contain very few active transporters that are mostly responsible for clearing small molecules out of the brain. The paracellular route (between cell junctions) is not available to small molecules, but only the transcellular route is (through cell membranes). Classically, molecules to target the brain, such as benzodiazepines, are hydrophobic to allow them to penetrate cell membranes. The instant invention is compatible with the search for chemical groups that confer protein resistant and alleviate the common problem of excessive protein binding associated with molecules such as the benzodiazepines; this requires high dosing to account for the large percentage of binding to serum proteins. The approaches described earlier for the identification of binders of PGP will be of help to optimize molecules for improved residence time in the brain.

Several model systems are available, employing monolayers of various cell types, for evaluation of active transport of pharmaceutically active substances. For example, monolayers of Caco-2 intestinal epithelial cells can be used to evaluate active transport of substances between the intestine and the bloodstream. When plated on a surface which allows the flow of material from apical to basolateral and vice versa, such cells form a biological membrane which can be used to simulate physiological absorption and bioavailability. In another example, mouse brain capillary endothelial cell (MBEC) lines have been established to evaluate active transport in and out of the central nervous system. Another example of such cells is HT29 human colon carcinoma cells. Further, monolayers expressing particular transporter proteins can be established using transfected cells. For example, Sasaki et al (2002) J. Biol. Chem. 8:6497 used a double-transfected Madin-Darby canine kidney cell monolayer to study transport of organic anions.

Alternatives to cell monolayers may of course be utilized to examine permeability. Alternatives typically comprise a biological structure capable of active transport and include, but are not limited to, organs of the digestive tract obtained from lab animals and reconstituted organs or membranes created in vitro from cells seeded in an artificial matrix.

In another aspect, the present invention provides pharmaceutically acceptable compositions which comprise a therapeutically-effective amount of one or more of the compounds of the present invention, including but not limited to the compounds described above and those shown in the Figures, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment, e.g. reasonable side effects applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals with toxicity, irritation, allergic response, or other problems or complications, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluene-sulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated foam, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage foams by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-. di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-monooleate, PEG-di-oleate, PEG-mono-laurate and di-laurate, Lecithin, Polysorbate 80, etc (produced and distributed by a number of companies in USA and worldwide).

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). The polymers used in the present invention have a significantly smaller molecular weight, approximately 100 daltons, compared to the large MW of 5000 daltons or greater that used in standard pegylation techniques. Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic® Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

The subject compounds may be synthesized using the methods of combinatorial synthesis described in this section. Combinatorial libraries of the compounds may be used for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; Chen et al. (1994) JACS 116: 2661: Kerr et al. (1993) JACS 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

The libraries of the subject method can take the multipin library format. Briefly, Geysen and co-workers (Geysen et al. (1984) PNAS 81:3998-4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) Tetrahedron Lett 31:5811-5814; Valerio et al. (1991) Anal Biochem 197:168-177; Bray et al. (1991) Tetrahedron Lett 32:6163-6166).

In yet another embodiment, a variegated library of compounds can be provided on a set of beads utilizing the strategy of divide-couple-recombine (see, e.g., Houghten (1985) PNAS 82:5131-5135; and U.S. Pat. Nos. 4,631,211; 5,440, 016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) PNAS 82:5131-5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) Annu Rep Med Chem 26:271-280; Fodor, S. P. A. (1991) Science 251:767; Pirrung et al. (1992) U.S. Pat. No. 5,143,854; Jacobs et al. (1994) Trends Biotechnol 12:19-26). The spatial resolution of photolithography affords miniaturization. This technique can be carried out through the use protection/deprotection reactions with photolabile protecting groups.

The key points of this technology are illustrated in Gallop et al. (1994) J Med Chem 37:1233-1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

The principle of using oligonucleotides to encode combinatorial synthetic libraries was described in 1992 (Brenner et al. (1992) PNAS 89:5381-5383), and an example of such a library appeared the following year (Needles et al. (1993) *PNAS* 90:10700-10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529-2531), orthogonality in synthesis is achieved by employing acid-labile protection for the coding strand and base-labile protection for the compound strand.

In an alternative approach (Nikolaiev et al. (1993) *Pept Res* 6:161-170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891-3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

An alternative form of encoding the test compound library employs a set of non-sequencable electrophoric tagging molecules that are used as a binary code (Ohlmeyer et al. (1993) *PNAS* 90:10922-10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723-4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027-6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXAMPLES

The invention now being generally described, it will be more readily understood by reference to the following examples, which are included merely for purposes of illustration of certain aspects and embodiments of the present invention, and are not intended to limit the invention.

General Process:

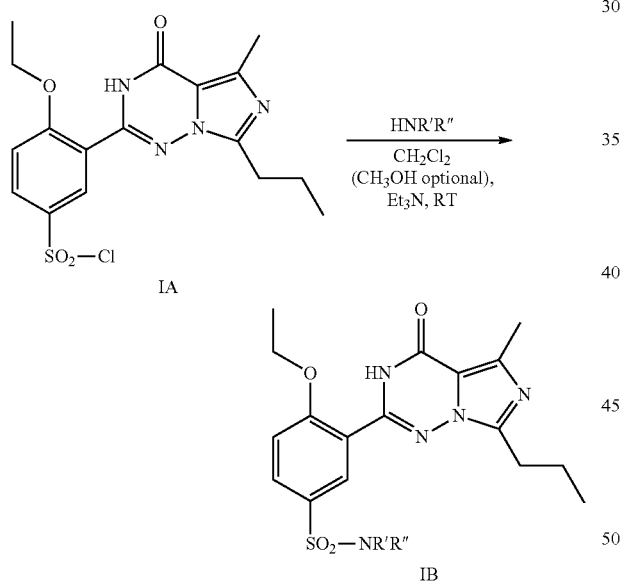

The compound IA is treated with the amine, HNR'R", in methylene chloride or in a mixture of methylene chloride and methanol (9:1), and triethylamine. The reaction mixture is stirred at room temperature.

To the reaction solution is added methylene chloride and water, and the layers are separated. The aqueous layer is extracted with methylene chloride. The combined organic layers are washed with 10% citric acid, water and brine and dried over sodium sulfate. For products having basic substituents (amines, etc.) saturated sodium bicarbonate solution may be substituted for the 10% citric acid. The dried organic portion is concentrated in vacuo is optionally purified by flash chromatography or by recrystallization.

Example 1

Compound 1

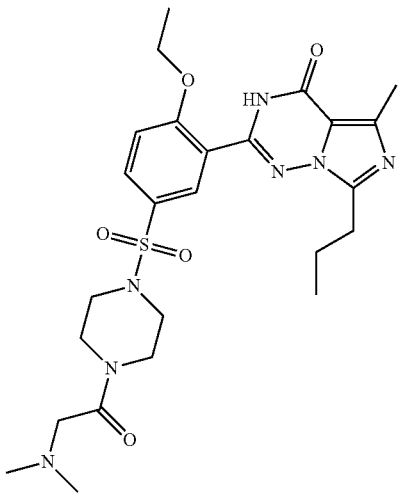

M.W. (calculated): 545.66
M.W. (mass spec.): 546.2

Example 2

Compound 2

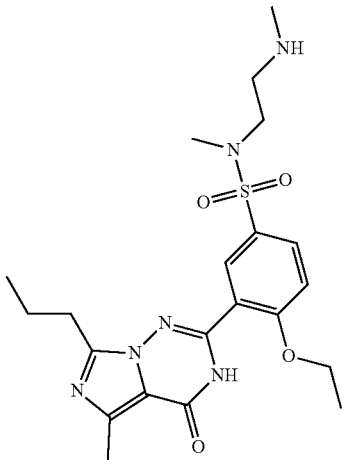

M.W. (calculated): 462.57
M.W. (mass spec.): 463.2

Example 3

Compound 3

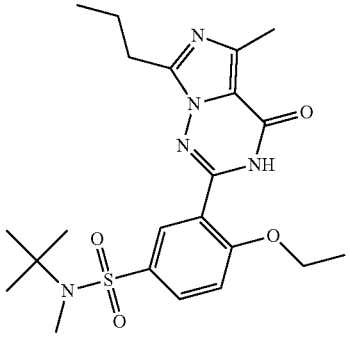

M.W. (calculated): 461.59
M.W. (mass spec.): 462.2

Example 4
Compound 4
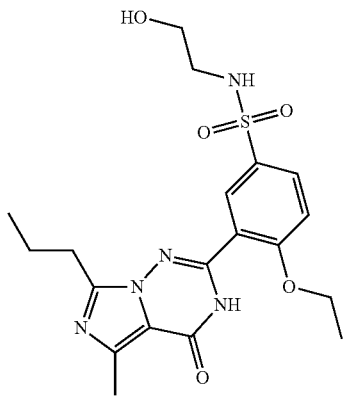
M.W. (calculated): 435.50
M.W. (mass spec.): 436.2
Example 5
Compound 5
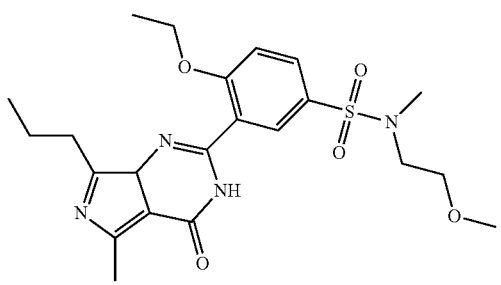
M.W. (calculated): 463.56
M.W. (mass spec.): 464.3
Example 6
Compound 6
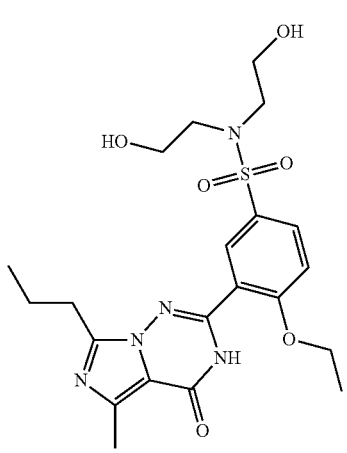
M.W. (calculated): 479.56
M.W. (mass spec.): 480.3
Example 7
Compound 7
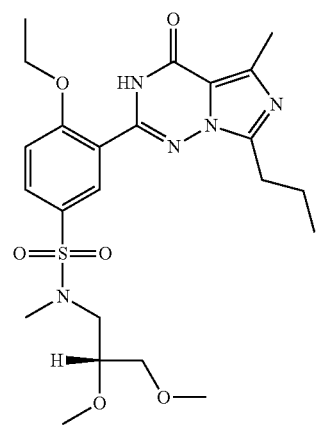
M.W. (calculated): 507.61
M.W. (mass spec.): 508.3
Example 8
Compound 8
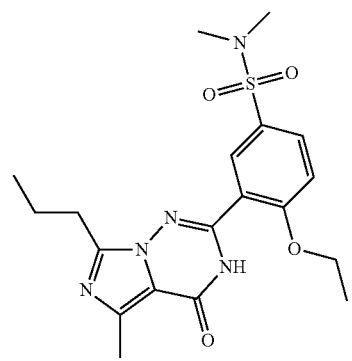
M.W. (calculated): 419.50
M.W. (mass spec.): 420.4
Example 9
Compound 9
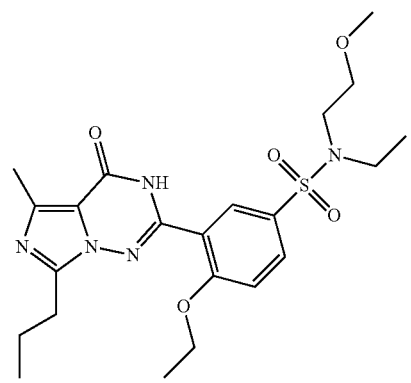
M.W. (calculated): 477.58
M.W. (mass spec.): 478.4

Example 10
Compound 10
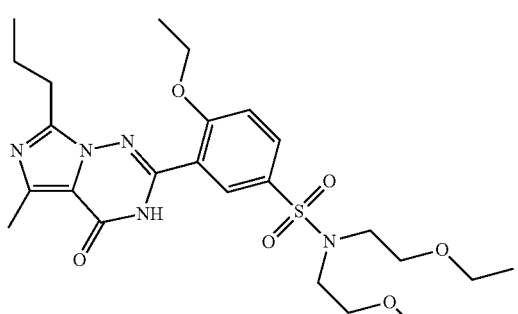
M.W. (calculated): 535.66
M.W. (mass spec): 536.4
Example 11
Compound 11
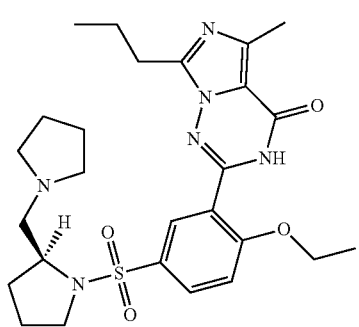
M.W. (calculated): 565.14
M.W. (mass spec.): 566.1
Example 12
Compound 12
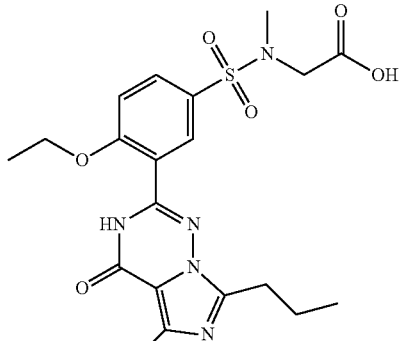
M.W. (calculated): 463.51
M.W. (mass spec.): 462.2
Example 13
Compound 13
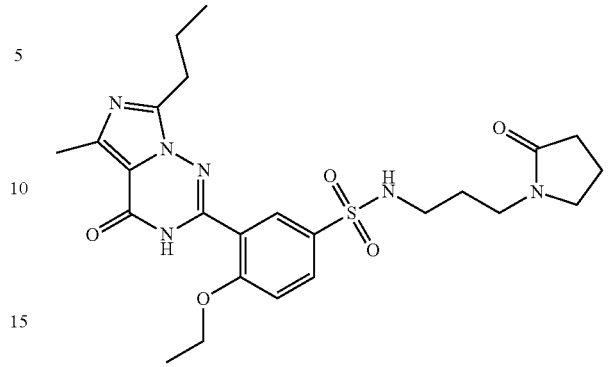
M.W. (calculated): 516.62
M.W. (mass spec.): 517.16
Example 14
Compound 14
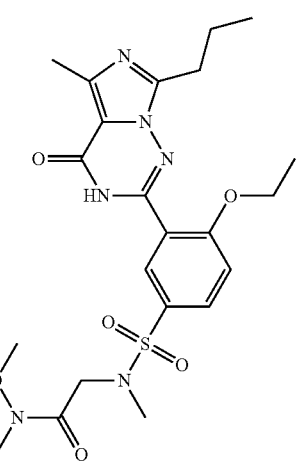
M.W. (calculated): 506.58
M.W. (mass spec.): 507.15
Example 15
Compound 15
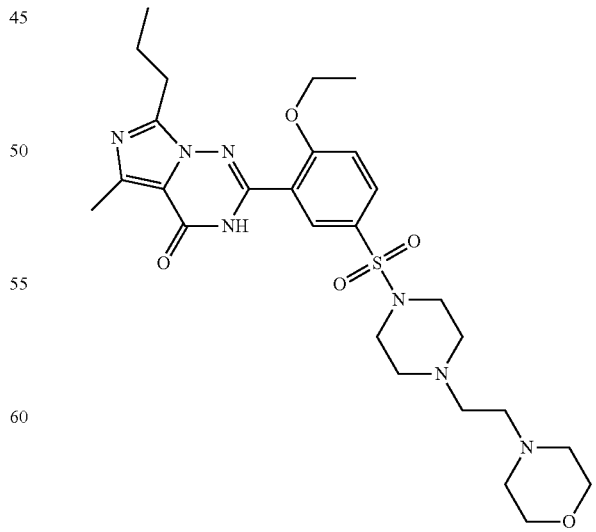
M.W. (calculated): 573.72
M.W. (mass spec.): 574.3

Example 16
Compound 16
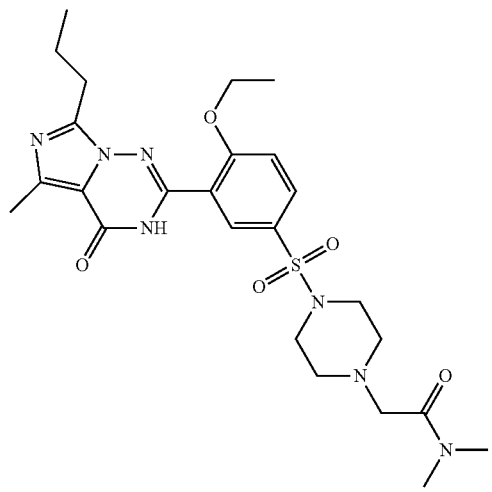
M.W. (calculated): 545.66
M.W. (mass spec.): 546.13
Example 17
Compound 17
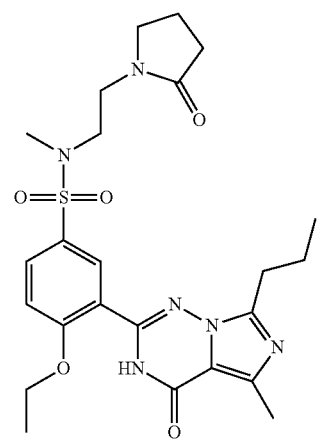
M.W. (calculated): 493.58
M.W. (mass spec.): 494.11
Example 18
Compound 18
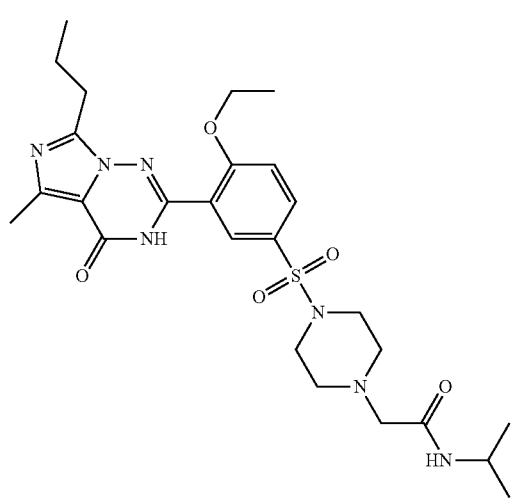
M.W. (calculated): 559.69
M.W. (mass spec.): 560.18
Example 19
Compound 19
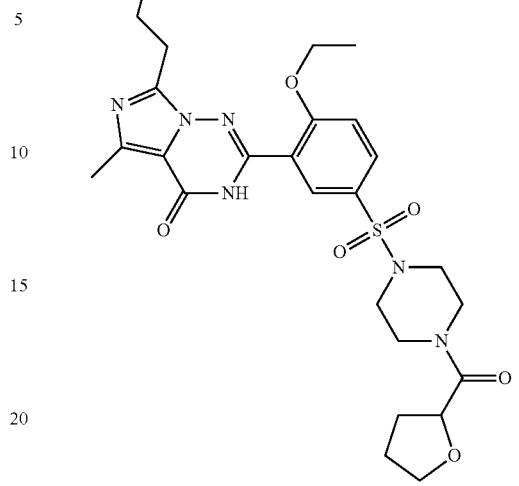
M.W. (calculated): 558.66
M.W. (mass spec.): 559.17
Example 20
Compound 20
M.W. (calculated): 516.62
M.W. (mass spec.): 517.29
Example 21
Compound 21
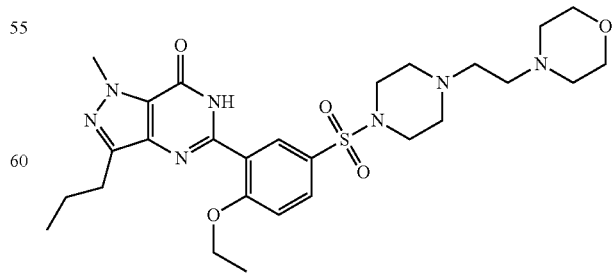
M.W. (calculated): 573.72

Example 22
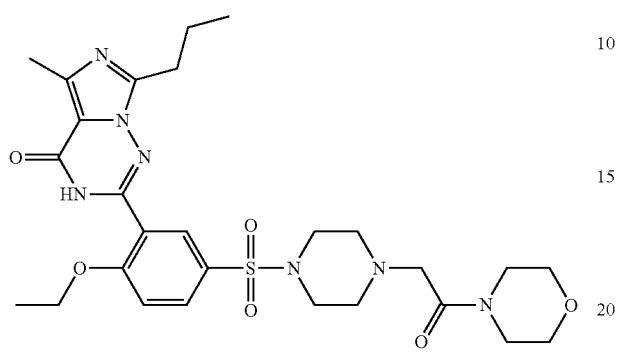
Compound 22
M.W. (calculated): 587.7
M.W. (mass spec.): 588.3
Example 23
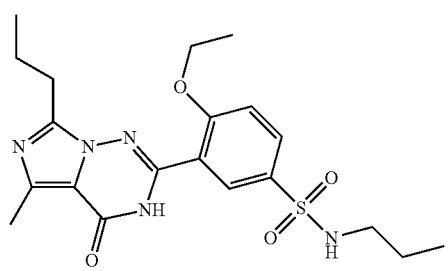
Compound 23
M.W. (calculated): 433.55
M.W. (mass spec.): 434.3
Example 24
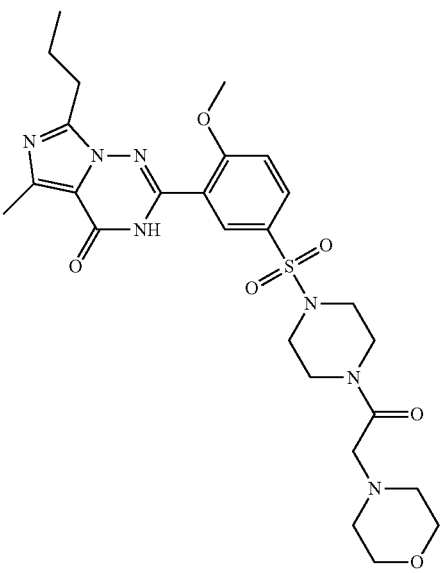
Compound 24
M.W. (calculated): 587.7
M.W. (mass spec.): 588.3
TABLE 1
| Compound No. | Molecular Weight | $IC_{50}$ (nM) |
| --- | --- | --- |
| 1 | 545.663 | 0.14 |
| 2 | 462.573 | 0.64 |
| 3 | 461.585 | 0.10 |
| 4 | 435.503 | 1.08 |
| 5 | 463.557 | 0.16 |
| 6 | 479.556 | 0.52 |
| 7 | 507.61 | 0.35 |
| 8 | 419.504 | 1.00 |
| 9 | 477.584 | 0.11 |
| 10 | 535.664 | 0.34 |
| 11 | 565.137 | 1.00 |
| 12 | 463.513 | 0.10 |
| 13 | 516.621 | 0.05 |
| 14 | 506.582 | 0.10 |
| 15 | 573.717 | 0.16 |
| 16 | 545.663 | 0.04 |
| 17 | 493.583 | 0.06 |
| 18 | 559.69 | 0.03 |
| 19 | 558.658 | 0.05 |
| 20 | 516.621 | 0.14 |
| 21 | 573.717 | 1.50 |
| 22 | 587.7 | 0.05 |
| 23 | 433.531 | 0.19 |
| 24 | 587.7 | 0.20 |
TABLE 2
| Compound No. | Caco-2 ($10^{-6}$ cm/s) | | PAMPA ($10^{-6}$ cm/s) | | Solubility (ug/mL) | | $T_{1/2}$ (min) liver microsomes | | Non-Spec Binding (%) | Protein Binding (%) |
| --- | --- | --- | --- | --- | --- | --- | --- | --- | --- | --- |
| | AtoB | BtoA | Hex | Lec | pH 7.4 | pH 2.7 | human | rat | | |
| 1 | | | ~1.06 | | 111.17 | 124.14 | 33.95 | 45.4 | | |
| 2 | 1.475 | 9.875 | 1.17 | 1.47 | >50 | >50 | | | | |
| 3 | 50.8 | 50.4 | 53.9 | | 15 | 90.15 | | | | |
| 4 | | | ~.0062 | 0.0019 | | | | | | |
| 5 | 51.85 | 56.25 | 78.19 | 7.14 | >50 | >50 | 19.3 | 12.34 | 23.64 | 97.4 |
| 6 | 4.3 | 28.1 | ~.08 | | | | | | | |
| 7 | 48.56 | 57.41 | 76.076 | | | | | | 25.5 | 98.2 |
| 8 | 45.4 | 47.4 | 68.92 | | | | | | 44.2 | 97.6 |
| 9 | 55.1 | 60.9 | 133.26 | | | | 9.83 | 9.8 | 35.85 | 99 |

TABLE 2-continued

| Compound | Caco-2 (10⁻⁶ cm/s) | | PAMPA (10⁻⁶ cm/s) | | Solubility (ug/mL) | | T$_{1/2}$ (min) liver microsomes | | Non-Spec Binding | Protein Binding |
|---|---|---|---|---|---|---|---|---|---|---|
| No. | AtoB | BtoA | Hex | Lec | pH 7.4 | pH 2.7 | human | rat | (%) | (%) |
| 10 | | | 48.97 | | | | | | 89.9 | 98.8 |
| 11 | 6.87 | 30.53 | 3.86 | | >50 | >50 | | | | |
| 12 | 2.2 | 5.5 | | | | | | | 0.8 | 97.5 |
| 13 | 10.6 | 36.67 | | | | | 12.66 | 16.58 | 5.95 | 91.15 |
| 14 | 20.62 | 48.75 | | | | | | | 9.9 | 97.6 |
| 15 | 8.45 | 40.65 | | | 110 | 115 | 30.76 | 34.03 | 8.78 | 84.48 |
| 16 | 2.65 | 45.35 | | | | | >60 | 59.85 | 9.72 | 89 |
| 17 | 40.48 | 39.44 | | | | | 1.08 | 6.83 | 36.5 | 98.4 |
| 18 | 4.11 | 46.29 | | | | | 44.08 | 32.99 | 22.15 | 90.55 |
| 19 | 7.86 | 44.82 | | | | | 22.43 | 23.99 | 15.5 | 89.55 |
| 20 | | | | | 90.9 | 93.3 | | | 7.4 | 96.3 |
| 21 | | | | | 26 | 111.5 | 47 | 34 | 68.4 | 92.9 |
| 22 | | | | | | | | | 0.8 | 88.45 |
| 23 | | | | | | | | | | |
| 24 | | | | | >116.7 | >124.4 | | | 6.6 | 84.5 |

TABLE 3

| Compound | PDE-1 | PDE-3 | PDE-4 human | PDE-5 human | PDE-6 bovine | Chronic Cytoxicity (mouse 3T3) | |
|---|---|---|---|---|---|---|---|
| No. | IC$_{50}$(M) | IC$_{50}$(M) | IC$_{50}$(M) | IC$_{50}$(M) | IC$_{50}$(M) | GI$_{50}$(M) | LC$_{50}$(M) |
| 1 | 9.50E−08 | | | 1.40E−10 | 4.40E−09 | | |
| 2 | 8.20E−08 | 1.93E−06 | | 6.46E−10 | 1.63E−08 | >7.5E−05 | >7.5E−05 |
| 3 | 1.19E−08 | 3.23E−07 | | 1.07E−10 | 3.74E−09 | >5.E−05 | >1.E−04 |
| 4 | 1.87E−08 | 2.03E−06 | | 1.08E−09 | 5.63E−09 | ~5.E−05 | >1.E−04 |
| 5 | 1.72E−08 | 1.29E−06 | 1.84E−06 | 1.63E−10 | 1.97E−09 | ~1.E−04 | >1.E−04 |
| 6 | 2.60E−08 | 1.50E−06 | | 5.20E−10 | 1.70E−08 | | |
| 7 | 1.47E−08 | 7.84E−07 | | 3.56E−10 | 2.90E−09 | | |
| 8 | 3.10E−08 | 1.20E−06 | | 1.00E−09 | 5.00E−09 | | |
| 9 | 1.29E−08 | 6.97E−07 | 1.12E−06 | 1.13E−10 | 9.46E−10 | 8.73E−05 | >1.E−04 |
| 10 | 1.20E−08 | 5.46E−07 | | 3.40E−10 | 2.60E−09 | | |
| 11 | 4.80E−08 | 2.10E−06 | | 1.00E−09 | 2.30E−08 | 2.50E−05 | >1.E−04 |
| 12 | 2.40E−08 | 1.30E−06 | 5.00E−06 | 1.00E−10 | 4.80E−10 | | |
| 13 | 3.50E−09 | 7.77E−07 | 3.73E−07 | 5.10E−11 | 6.45E−10 | | |
| 14 | 1.20E−08 | 6.48E−07 | 1.55E−06 | 1.04E−10 | 2.90E−09 | | |
| 15 | 4.63E−08 | 2.23E−06 | 3.69E−06 | 1.60E−10 | 1.09E−09 | | |
| 16 | 1.70E−08 | 9.41E−07 | 9.63E−07 | 4.00E−11 | 3.65E−10 | | |
| 17 | 2.60E−09 | 3.91E−07 | 1.10E−06 | 6.60E−11 | 8.60E−10 | | |
| 18 | 1.60E−08 | 5.07E−07 | 1.30E−06 | 3.70E−11 | 6.40E−10 | | |
| 19 | 2.55E−09 | 1.20E−06 | 6.86E−07 | 5.60E−11 | 6.85E−10 | | |
| 20 | 1.15E−08 | 1.17E−06 | 9.44E−07 | 1.35E−10 | 6.30E−10 | | |
| 21 | 7.60E−08 | 9.60E−06 | 3.70E−06 | 1.50E−09 | 1.20E−08 | | |
| 22 | 1.85E−08 | 5.11E−07 | 2.95E−06 | 5.00E−11 | 9.20E−10 | | |
| 23 | 1.50E−08 | 3.70E−06 | 2.30E−06 | 1.90E−10 | 6.20E−10 | | |
| 24 | 9.30E−09 | 4.00E−06 | 4.30E−06 | 2.00E−10 | 1.30E−09 | | |

INCORPORATION BY REFERENCE

All of the patents and publications cited herein are hereby incorporated by reference in their entireties.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A compound of the formula A:

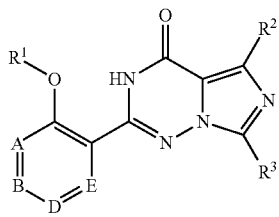

(A)

or a pharmaceutically acceptable salt, stereoisomer, or hydrate thereof, wherein $R^1$ is selected from lower alkyl;

$R^2$ is selected from lower alkyl, lower alkenyl and lower alkynyl, wherein the lower alkyl, lower alkenyl, and lower alkynyl may be optionally substituted with one or more halogen, lower alkoxy, hydroxy, CN, NO$_2$, amino, acylamino, amido, alkylthio, and —X—C(═O)—R or —C(═O)X—R, wherein X is a bond or oxygen or sulfur and R is H, alkyl, alkenyl, alkynyl, aralkyl, aryl, or a heterocyclic group;

$R^3$ is selected from $C_1$-$C_4$ alkyl, lower alkenyl and lower alkynyl, wherein the $C_1$-$C_4$ alkyl, lower alkenyl, and lower alkynyl may be optionally substituted with one or more halogen, lower alkoxy, hydroxy, CN, NO$_2$, amino, acylamino, amido, alkylthio, and —X—C(═O)—R or —C(═O)X—R, wherein X is a bond or oxygen or sulfur and R is H, alkyl, alkynyl, aralkyl, aryl, or a heterocyclic group;

A is N or C—H;

B is N, C—H, C—(SO$_2$—R$^4$), or C—CO—R$^4$;

D is N, C—H, C—(SO$_2$—R$^4$) or C—CO—R$^4$;

E is N or C—H;

wherein only one of A, B or E is N, and one of B or D is C—(SO$_2$—R$^4$) or C—CO—R$^4$;

R$^4$ is a group having the formula:

—NH—R$^{41}$,

—N(R$^{42}$)(R$^{43}$),

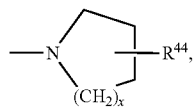 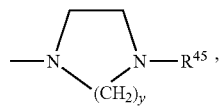

or

—N(R$^{46}$)$_2$;

R$^{41}$ is selected from straight-chain C$_3$-C$_6$ alkyl, branched-chain C$_3$-C$_6$ alkyl, C$_2$-C$_3$ alkyl-OH, —(CH$_2$)$_a$—N(H)(R$^{51}$) and —(CH$_2$)$_a$—N(R$^{52}$)(R$^{53}$);

R$^{51}$ is selected from C$_4$-C$_6$ alkyl, cycloalkyl, cycloalkenyl, alkyl-O-alkyl, alkyl-O-aryl, alkenyl, alkynyl, aralkyl, aryl and a heterocyclic group;

R$^{52}$ and R$^{53}$ are taken together with the nitrogen to which they are attached to form a 5- to 7-membered ring which is substituted at a ring carbon with one or two oxo groups and which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group, a is 1 to 6;

R$^{42}$ is selected from straight-chain alkyl, branched-chain alkyl, and C$_2$-C$_6$ alkyl-O-alkyl-;

R$^{43}$ is selected from C$_4$-C$_6$ alkyl, C$_2$-C$_6$ alkyl-NH-alkyl, C$_2$-C$_6$ alkyl-O-alkyl, alkyl-CO$_2$H, C$_2$-C$_6$ alkyl-CH(O-alkyl)(O-alkyl), C$_2$-C$_6$ alkyl-CH(O-alkyl)-alkyl-O-alkyl, —(CH$_2$)$_a$—N(H)(R$^{51}$), and —(CH$_2$)$_a$—N(R$^{52}$)(R$^{53}$);

R$^{44}$ is selected from the group consisting of —(CH$_2$)$_q$—N(R$^{12}$)(R$^{13}$), —(CH$_2$)$_r$—N(R$^{11}$)—(CH$_2$)$_s$C(O)R$^{14}$, —(CH$_2$)$_q$—C(O)R$^{14}$, —(CH$_2$)$_r$—C(O)—(CH$_2$)$_s$OR$^{11}$, —(CH$_2$)$_r$—C(O)—(CH$_2$)$_s$N(R$^{12}$)(R$^{13}$), and —(CH$_2$)$_r$O—(CH$_2$)$_s$—C(O)R$^{14}$, each R$^{11}$ is independently selected from H, C$_3$-C$_6$ alkyl, alkyl-O-alkyl, alkyl-O-aryl, alkenyl, alkynyl, cycloalkyl, cycloalkenyl, aralkyl, aryl and a heterocyclic group;

each R$^{12}$ and R$^{13}$ are independently selected from H, C$_2$-C$_6$ alkyl, cycloalkyl, cycloalkenyl, alkyl-O-alkyl, alkyl-O-aryl, alkenyl, alkynyl, aralkyl, aryl and a heterocyclic group; or R$^{12}$ and R$^{13}$ may be taken together with the nitrogen to which they are attached form a 5- to 7-membered ring which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group;

each R$^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

q is 1 to 6:

r is 0 to 6;

s is 0 to 6;

R$^{45}$ is selected from the group consisting of —(CH$_2$)$_v$—N(R$^{25}$)(R$^{26}$), —(CH$_2$)$_v$—N(R$^{21}$)—(CH$_2$)$_w$—C(O)R$^{24}$, —(CH$_2$)$_v$—C(O)R$^{24}$, —(CH$_2$)$_t$—C(O)—(CH$_2$)$_w$OR$^{21}$, —(CH$_2$)$_t$—C(O)(CH$_2$)$_w$—N(R$^{22}$)(R$^{23}$), and —(CH$_2$)$_v$—O—(CH$_2$)$_w$—C(O)R$^{24}$;

each R$^{21}$ is independently selected from H, C$_5$-C$_6$ alkyl, alkyl-O-alkyl, alkyl-O-aryl, alkenyl, alkynyl, cycloalkyl, cycloalkenyl, aralkyl, aryl and a heterocyclic group;

each R$^{22}$ and R$^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or R$^{22}$ and R$^{23}$ may be taken together with the nitrogen to which they are attached form a 5- to 7-membered ring which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group, each R$^{24}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

R$^{25}$ and R$^{26}$ taken together with the nitrogen to which they are attached form a 5- to 7-membered ring which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group;

t is 0 to 6;

v is 1 to 6;

w is 0 to 6;

x is 1 or 2;

y is 1 or 2; and

R$^{46}$ are both selected from C$_2$-C$_6$ alkyl-O—C$_2$-C$_6$ alkyl.

2. The compound of claim 1, having the formula A$^1$:

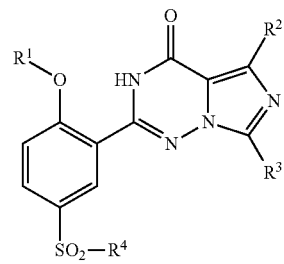

(A$^1$)

or a pharmaceutically acceptable salt, stereoisomer, or hydrate thereof, wherein R$^1$ is selected from lower alkyl;

R$^2$ is selected from lower alkyl, and lower alkenyl and lower alkynyl, wherein the lower alkyl, lower alkenyl, and lower alkynyl may be optionally substituted with one or more halogen, lower alkoxy, hydroxy, CN, NO$_2$, amino, acylamino, amido, alkylthio, and —X—C(=O)—R or —C(=O)X—R, wherein X is a bond or oxygen or sulfur and R is H, alkyl, alkenyl, alkynyl, aralkyl, aryl, or a heterocyclic group;

$R^3$ is selected from $C_1$-$C_4$ alkyl, lower alkenyl and lower alkynyl, wherein the $C_1$-$C_4$ alkyl, lower alkenyl, and lower alkynyl may be optionally substituted with one or more halogen, lower alkoxy, hydroxy, CN, $NO_2$, amino, acylamino, amido, alkylthio, and —X—C(═O)—R or —C(═O)X—R, wherein X is a bond or oxygen or sulfur and R is H, alkyl, alkynyl, aralkyl, aryl, or a heterocyclic group;

$R^4$ is a group having the formula:
—NH—$R^{41}$,
—N($R^{42}$)($R^{43}$),

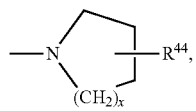 , 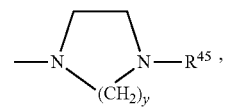

or
—N($R^{46}$)$_2$;

$R^{41}$ is selected from straight-chain $C_3$-$C_6$ alkyl, branched-chain $C_3$-$C_6$ alkyl, $C_2$-$C_3$alkyl-OH, —(CH$_2$)$_a$—N(H)($R^{51}$) and —(CH$_2$)$_a$—N($R^{52}$)($R^{53}$);

$R^{51}$ is selected from $C_4$-$C_6$ alkyl, cycloalkyl, cycloalkenyl, alkyl-O-alkyl, alkyl-O-aryl, alkenyl, alkynyl, aralkyl, aryl and a heterocyclic group;

$R^{52}$ and $R^{53}$ are taken together with the nitrogen to which they are attached to form a 5- to 7-membered ring which is substituted at a ring carbon with one or two oxo groups and which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group, a is 1 to 6;

$R^{42}$ is selected from straight-chain alkyl, branched-chain alkyl, and $C_2$-$C_6$ alkyl-O-alkyl-;

$R^{43}$ is selected from $C_4$-$C_6$ alkyl, $C_2$-$C_6$ alkyl-NH-alkyl, $C_2$-$C_6$ alkyl-O-alkyl, alkyl-$CO_2$H, $C_2$-$C_6$ alkyl-CH(O-alkyl)(O-alkyl), $C_2$-$C_6$ alkyl-CH(O-alkyl)-alkyl-O-alkyl, —(CH$_2$)$_a$—N(H)($R^{51}$), and —(CH$_2$)$_a$—N($R^{52}$)($R^{53}$);

$R^{44}$ is selected from the group consisting of
—(CH$_2$)$_q$—N($R^{12}$)($R^{13}$), —(CH$_2$)$_r$—N($R^{11}$)—(CH$_2$)$_s$C(O)$R^{14}$, —(CH$_2$)$_q$—C(O)$R^{14}$,
—(CH$_2$)$_r$—C(O)—(CH$_2$)$_s$OR$^{11}$, —(CH$_2$)$_r$—C(O)—(CH$_2$)$_s$N($R^{12}$)($R^{13}$), and
—(CH$_2$)$_r$—O—(CH$_2$)$_s$—C(O)$R^{14}$, each $R^{11}$ is independently selected from H, $C_3$-$C_6$ alkyl, alkyl-O-alkyl, alkyl-O-aryl, alkenyl, alkynyl, cycloalkyl, cycloalkenyl, aralkyl, aryl and a heterocyclic group;

each $R^{12}$ and $R^{13}$ are independently selected from H, $C_2$-$C_6$ alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

q is 1 to 6:
r is 0 to 6;
s is 0 to 6;

$R^{45}$ is selected from the group consisting of
-(CH$_2$)$_v$—N($R^{25}$)($R^{26}$), —(CH$_2$)$_v$—N($R^{21}$)—(CH$_2$)$_w$—C(O)$R^{24}$, —(CH$_2$)$_v$—C(O)$R^{24}$,
—(CH$_2$)$_t$—C(O)—(CH$_2$)$_w$OR$^{21}$, —(CH$_2$)$_t$—C(O)(CH$_2$)$_w$—N($R^{22}$)($R^{23}$), and
—(CH$_2$)$_v$—O—(CH$_2$)$_w$—C(O)$R^{24}$;

each $R^{21}$ is independently selected from H, $C_5$-$C_6$ alkyl, alkyl-O-alkyl, alkyl-O-aryl, alkenyl, alkynyl, cycloalkyl, cycloalkenyl, aralkyl, aryl and a heterocyclic group;

each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group, each $R^{24}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

$R^{25}$ and $R^{26}$ taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

t is 0 to 6;
v is 1 to 6;
w is 0 to 6;
x is 1 or 2;
y is 1 or 2; and
$R^{46}$ are both selected from $C_2$-$C_6$ alkyl-O—$C_2$-$C_6$ alkyl.

3. The compound of claim 2, having the formula $A_2$:

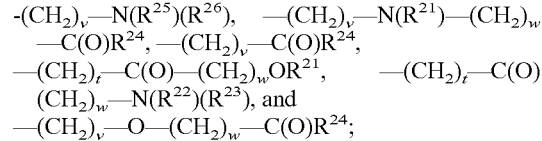

(A$_2$)

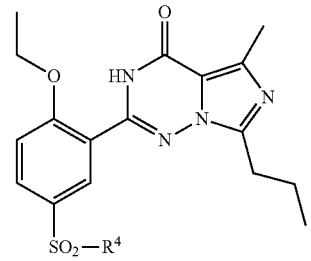

or a pharmaceutically acceptable salt or stereoisomer thereof, wherein
$R^4$ is a group having the formula:

—NH—$R^{41}$,

—N($R^{42}$)($R^{43}$),

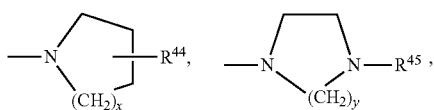

or

$R^{41}$ is selected from straight-chain $C_3$-$C_6$ alkyl, branched-chain $C_3$-$C_6$ alkyl, $C_2$-$C_3$alkyl-OH, —$(CH_2)_a$—N(H)($R^{51}$) and —$(CH_2)_a$—N($R^{52}$)($R^{53}$);

$R^{51}$ is selected from $C_4$-$C_6$ alkyl, cycloalkyl, cycloalkenyl, alkyl-O-alkyl, alkyl-O-aryl, alkenyl, alkynyl, aralkyl, aryl and a heterocyclic group;

$R^{52}$ and $R^{53}$ are taken together with the nitrogen to which they are attached to form a 5- to 7-membered ring which is substituted at a ring carbon with one or two oxo groups and which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group, a is 1 to 6;

$R^{42}$ is selected from straight-chain alkyl, branched-chain alkyl, and $C_2$-$C_6$ alkyl-O-alkyl-;

$R^{43}$ is selected from $C_4$-$C_6$ alkyl, $C_2$-$C_6$ alkyl-NH-alkyl, $C_2$-$C_6$ alkyl-O-alkyl, alkyl-$CO_2$H, $C_2$-$C_6$ alkyl-CH(O-alkyl)(O-alkyl), $C_2$-$C_6$ alkyl-CH(O-alkyl)-alkyl-O-alkyl, —$(CH_2)_a$—N(H)($R^{51}$), and —$(CH_2)_a$—N($R^{52}$)($R^{53}$);

$R^{44}$ is selected from the group consisting of
—$(CH_2)_q$—N($R^{12}$)($R^{13}$), —$(CH_2)_r$—N($R^{11}$)—$(CH_2)_s$C(O)$R^{14}$, —$(CH_2)_q$—C(O)$R^{14}$,
—$(CH_2)_r$—C(O)—$(CH_2)_s$O$R^{11}$, —$(CH_2)_r$—C(O)—$(CH_2)_s$N($R^{12}$)($R^{13}$), and
—$(CH_2)_r$O—$(CH_2)_s$—C(O)$R^{14}$, each $R^{11}$ is independently selected from H, $C_3$-$C_6$ alkyl, alkyl-O-alkyl, alkyl-O-aryl, alkenyl, alkynyl, cycloalkyl, cycloalkenyl, aralkyl, aryl and a heterocyclic group;

each $R^{12}$ and $R^{13}$ are independently selected from H, $C_2$-$C_6$ alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

q is 1 to 6:
r is 0 to 6;
s is 0 to 6;

$R^{45}$ is selected from the group consisting of
—$(CH_2)_v$—N($R^{25}$)($R^{26}$), —$(CH_2)_v$—N($R^{21}$)—$(CH_2)_w$—C(O)$R^{24}$, —$(CH_2)_v$—C(O)$R^{24}$,
—$(CH_2)_t$—C(O)—$(CH_2)_w$O$R^{21}$, —$(CH_2)_t$—C(O)($CH_2)_w$—N($R^{22}$)($R^{23}$), and
—$(CH_2)_v$—O—$(CH_2)_w$—C(O)$R^{24}$;

each $R^{21}$ is independently selected from H, $C_5$-$C_6$ alkyl, alkyl-O-alkyl, alkyl-O-aryl, alkenyl, alkynyl, cycloalkyl, cycloalkenyl, aralkyl, aryl and a heterocyclic group;

each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group, each $R^{24}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

$R^{25}$ and $R^{26}$ taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group;

t is 0 to 6;
v is 1 to 6;
w is 0 to 6;
x is 1 or 2;
y is 1 or 2; and
$R^{46}$ are both selected from $C_2$-$C_6$ alkyl-O—$C_2$-$C_6$ alkyl.

4. The compound of claim 1, having the formula $B_1$:

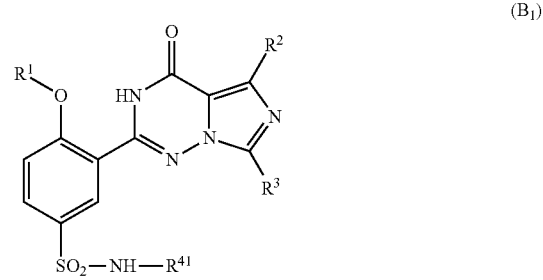

(B₁)

wherein,
or a pharmaceutically acceptable salt, stereoisomer, or hydrate thereof, wherein $R^1$ is selected from lower alkyl;

$R^2$ is selected from lower alkyl, and lower alkenyl and lower alkynyl, wherein the lower alkyl, lower alkenyl, and lower alkynyl may be optionally substituted with one or more halogen, lower alkoxy, hydroxy, CN, $NO_2$, amino, acylamino, amido, alkylthio, and —X—C(=O)—R or —C(=O)X—R, wherein X is a bond or oxygen or sulfur and R is H, alkyl, alkenyl, alkynyl, aralkyl, aryl, or a heterocyclic group;

$R^3$ is selected from $C_1$-$C_4$ alkyl, lower alkenyl and lower alkynyl, wherein the $C_1$-$C_4$ alkyl, lower alkenyl, and lower alkynyl may be optionally substituted with one or more halogen, lower alkoxy, hydroxy, CN, $NO_2$, amino, acylamino, amido, alkylthio, and —X—C(=O)—R or —C(=O)X—R, wherein X is a bond or oxygen or sulfur and R is H, alkyl, alkynyl, aralkyl, aryl, or a heterocyclic group;

$R^{41}$ is selected from straight-chain $C_3$-$C_6$ alkyl, branched-chain $C_3$-$C_6$ alkyl, $C_2$-$C_3$alkyl-OH, —$(CH_2)_a$—N(H)($R^{51}$) and —$(CH_2)_a$—N($R^{52}$)($R^{53}$);

$R^{51}$ is selected from $C_4$-$C_6$ alkyl, cycloalkyl, cycloalkenyl, alkyl-O-alkyl, alkyl-O-aryl, alkenyl, alkynyl, aralkyl, aryl and a heterocyclic group;

$R^{52}$ and $R^{53}$ are taken together with the nitrogen to which they are attached to form a 5- to 7-membered ring which is substituted at a ring carbon with one or two oxo groups and which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group, and a is 1 to 6.

5. The compound of claim 4, having the formula $B_2$:

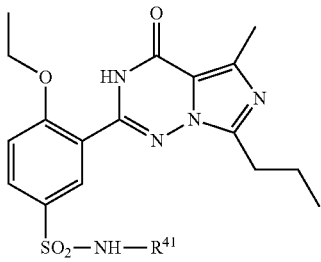

(B₂)

wherein, $R^{41}$ is selected from straight-chain $C_3$-$C_6$ alkyl, branched-chain $C_3$-$C_6$ alkyl, $C_2$-$C_3$alkyl-OH, —$(CH_2)_a$—N(H)($R^{51}$) and —$(CH_2)_a$—N($R^{52}$)($R^{53}$);

$R^{51}$ is selected from $C_4$-$C_6$ alkyl, cycloalkyl, cycloalkenyl, alkyl-O-alkyl, alkyl-O-aryl, alkenyl, alkynyl, aralkyl, aryl and a heterocyclic group;

$R^{52}$ and $R^{53}$ are taken together with the nitrogen to which they are attached to form a 5- to 7-membered ring which is substituted at a ring carbon with one or two oxo groups and which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group, and a is 1 to 6.

6. The compound of claim 1, having a structure selected from the group consisting of:

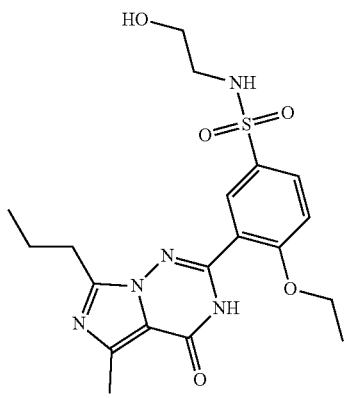

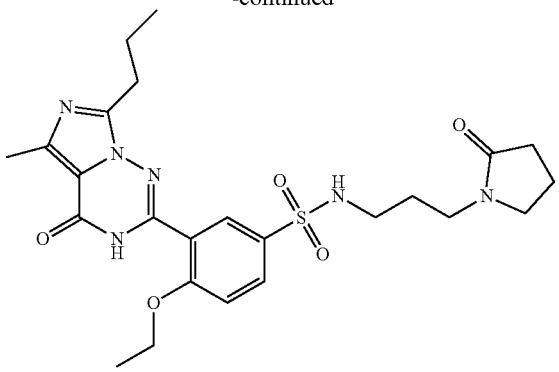

and

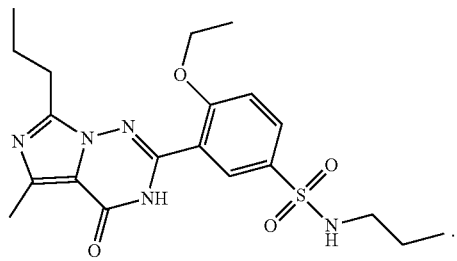

7. The compound of claim 1, having the formula $C_1$:

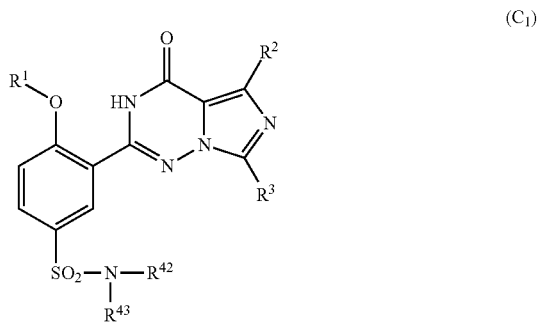

(C₁)

or a pharmaceutically acceptable salt, stereoisomer, or hydrate thereof, wherein $R^1$ is selected from lower alkyl;

$R^2$ is selected from lower alkyl, and lower alkenyl and lower alkynyl, wherein the lower alkyl, lower alkenyl, and lower alkynyl may be optionally substituted with one or more halogen, lower alkoxy, hydroxy, CN, $NO_2$, amino, acylamino, amido, alkylthio, and —X—C(=O)—R or —C(=O)X—R, wherein X is a bond or oxygen or sulfur and R is H, alkyl, alkenyl, alkynyl, aralkyl, aryl, or a heterocyclic group;

$R^3$ is selected from $C_1$-$C_4$ alkyl, lower alkenyl and lower alkynyl, wherein the $C_1$-$C_4$ alkyl, lower alkenyl, and lower alkynyl may be optionally substituted with one or more halogen, lower alkoxy, hydroxy, CN, $NO_2$, amino, acylamino, amido, alkylthio, and —X—C(=O)—R or —C(=O)X—R, wherein X is a bond or oxygen or sulfur and R is H, alkyl, alkynyl, aralkyl, aryl, or a heterocyclic group;

$R^{42}$ is selected from straight-chain alkyl, branched-chain alkyl, and $C_2$-$C_6$ alkyl-O-alkyl-; and $R^{43}$ is selected from $C_4$-$C_6$ alkyl, $C_2$-$C_6$ alkyl-NH-alkyl, $C_2$-$C_6$ alkyl-O-alkyl, alkyl-$CO_2$H, $C_2$-$C_6$ alkyl-CH(O- alkyl)(O-alkyl), $C_2$-$C_6$ alkyl-CH(O-alkyl)-alkyl-O-alkyl, —$(CH_2)_a$—N(H)($R^{51}$), and —$(CH_2)_a$—N($R^{52}$)($R^{53}$).

8. The compound of claim 7, having the formula $C_2$:

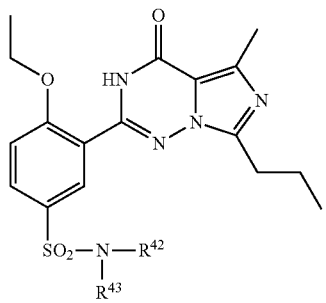

(C₂)

or a pharmaceutically acceptable salt, stereoisomer, or hydrate thereof, wherein $R^{42}$ is selected from straight-chain alkyl, branched-chain alkyl, and $C_2$-$C_6$ alkyl-O-alkyl-; and $R^{43}$ is selected from $C_4$-$C_6$ alkyl, $C_2$-$C_6$ alkyl-NH-alkyl, $C_2$-$C_6$ alkyl-O-alkyl, alkyl-$CO_2$H, $C_2$-$C_6$ alkyl-CH(O-alkyl)(O-alkyl), $C_2$-$C_6$ alkyl-CH(O-alkyl)-alkyl-O-alkyl, —$(CH_2)_a$—N(H)($R^{51}$), and —$(CH_2)_a$—N($R^{52}$)($R^{53}$).

9. A compound having a structure selected from the group consisting of:

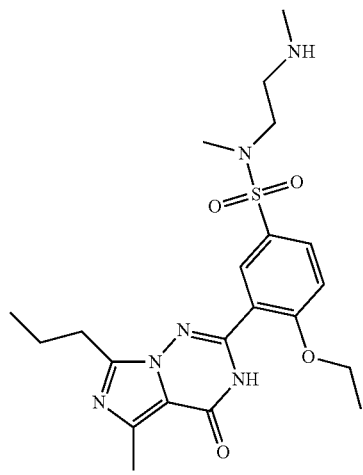

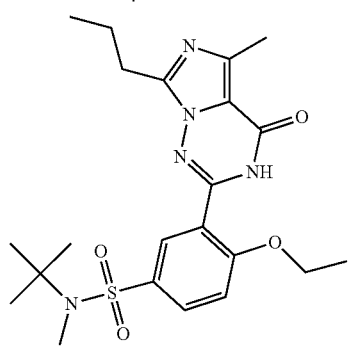

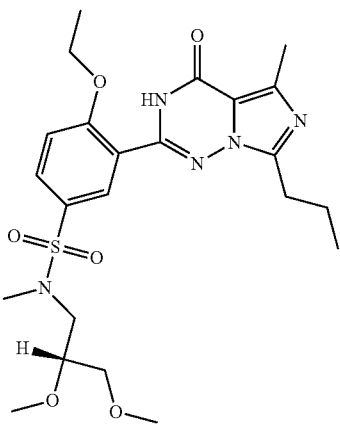

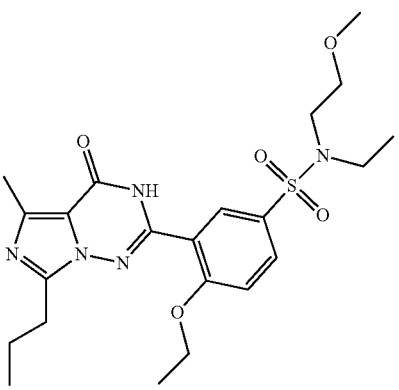

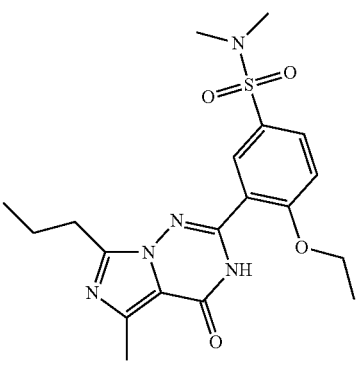

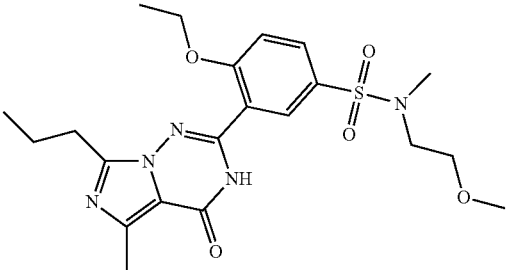

-continued

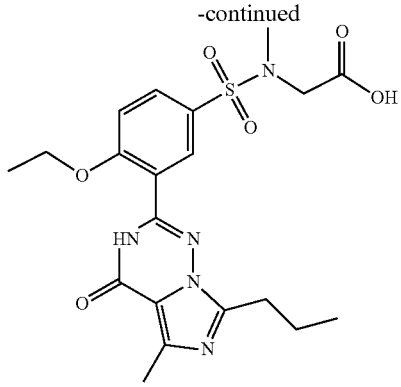

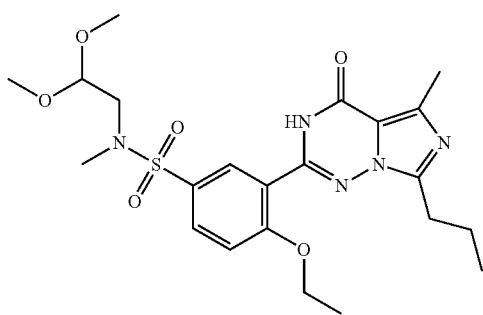

and

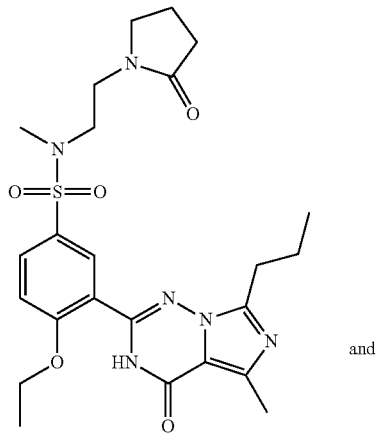

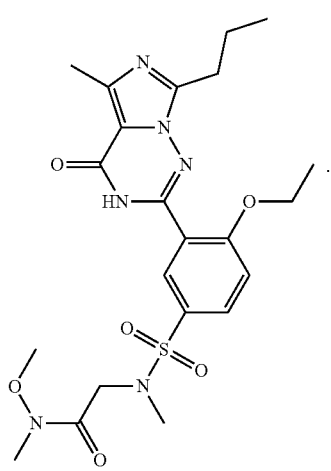 [SMILES: CCCc1nc(C)c2c(=O)[nH]c(-c3cc(S(=O)(=O)N(C)CC(=O)N(C)OC)ccc3OCC)nn12]

10. The compound of claim 1, having the formula $D_1$:

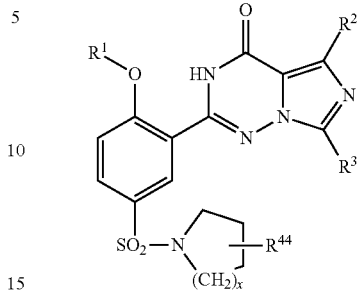

(D$_1$)

or a pharmaceutically acceptable salt, stereoisomer, or hydrate thereof, wherein $R^1$ is selected from lower alkyl;

$R^2$ is selected from lower alkyl, and lower alkenyl and lower alkynyl, wherein the lower alkyl, lower alkenyl, and lower alkynyl may be optionally substituted with one or more halogen, lower alkoxy, hydroxy, CN, NO$_2$, amino, acylamino, amido, alkylthio, and —X—C(=O)—R or —C(=O)X—R, wherein X is a bond or oxygen or sulfur and R is H, alkyl, alkenyl, alkynyl, aralkyl, aryl, or a heterocyclic group;

$R^3$ is selected from $C_1$-$C_4$ alkyl, lower alkenyl and lower alkynyl, wherein the $C_1$-$C_4$ alkyl, lower alkenyl, and lower alkynyl may be optionally substituted with one or more halogen, lower alkoxy, hydroxy, CN, NO$_2$, amino, acylamino, amido, alkylthio, and —X—C(=O)—R or —C(=O)X—R, wherein X is a bond or oxygen or sulfur and R is H, alkyl, alkynyl, aralkyl, aryl, or a heterocyclic group;

$R^{44}$ is selected from the group consisting of
—(CH$_2$)$_q$—N(R$^{12}$)(R$^{13}$), —(CH$_2$)$_r$—N(R$^{11}$)—(CH$_2$)$_s$C(O)R$^{14}$, —(CH$_2$)$_q$—C(O)R$^{14}$,
—(CH$_2$)$_r$C(O)—(CH$_2$)$_s$OR$^{11}$, —(CH$_2$)$_r$—C(O)—(CH$_2$)$_s$N(R$^{12}$)(R$^{13}$), and
—(CH$_2$)$_r$O—(CH$_2$)$_s$—C(O)R$^{14}$, each $R^{11}$ is independently selected from H, $C_3$-$C_6$ alkyl, alkyl-O-alkyl, alkyl-O-aryl, alkenyl, alkynyl, cycloalkyl, cycloalkenyl, aralkyl, aryl and a heterocyclic group;

each $R^{12}$ and $R^{13}$ are independently selected from H, $C_2$-$C_6$ alkyl, cycloalkyl, cycloalkenyl, alkyl-O-alkyl, alkyl-O-aryl, alkenyl, alkynyl, aralkyl, aryl and a heterocyclic group; or $R^{12}$ and $R^{13}$ may be taken together with the nitrogen to which they are attached form a 5- to 7-membered ring which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group;

each $R^{14}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

q is 1 to 6;
r is 0 to 6;
s is 0 to 6; and
x is 1 or 2.

11. The compound of claim 10, having the formula D₂:

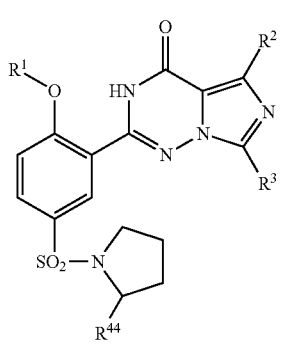

or a pharmaceutically acceptable salt, stereoisomer, or hydrate thereof, wherein R¹ is selected from lower alkyl;
R² is selected from lower alkyl, and lower alkenyl and lower alkynyl, wherein the lower alkyl, lower alkenyl, and lower alkynyl may be optionally substituted with one or more halogen, lower alkoxy, hydroxy, CN, NO₂, amino, acylamino, amido, alkylthio, and —X—C(=O)—R or —C(=O)X—R, wherein X is a bond or oxygen or sulfur and R is H, alkyl, alkenyl, alkynyl, aralkyl, aryl, or a heterocyclic group;
R³ is selected from C₁-C₄ alkyl, lower alkenyl and lower alkynyl, wherein the C₁-C₄ alkyl, lower alkenyl, and lower alkynyl may be optionally substituted with one or more halogen, lower alkoxy, hydroxy, CN, NO₂, amino, acylamino, amido, alkylthio, and —X—C(=O)—R or —C(=O)X—R, wherein X is a bond or oxygen or sulfur and R is H, alkyl, alkynyl, aralkyl, aryl, or a heterocyclic group;
R⁴⁴ is selected from the group consisting of
—(CH₂)_q—N(R¹²)(R¹³), —(CH₂)_r—N(R¹¹)—(CH₂)_s C(O)R¹⁴, —(CH₂)_q—C(O)R¹⁴,
—(CH₂)_rC(O)—(CH₂)_sOR¹¹, —(CH₂)_r—C(O)—(CH₂)_sN(R¹²)(R¹³), and
—(CH₂)_rO—(CH₂)_s—C(O)R¹⁴,
each R¹¹ is independently selected from H, C₃-C₆ alkyl, alkyl-O-alkyl, alkyl-O-aryl, alkenyl, alkynyl, cycloalkyl, cycloalkenyl, aralkyl, aryl and a heterocyclic group;
each R¹² and R¹³ are independently selected from H, C₂-C₆ alkyl, cycloalkyl, cycloalkenyl, alkyl-O-alkyl, alkyl-O-aryl, alkenyl, alkynyl, aralkyl, aryl and a heterocyclic group; or R¹² and R¹³ may be taken together with the nitrogen to which they are attached form a 5- to 7-membered ring which may optionally contain a further heteroatom and may be optionally substituted with up to three substituents selected from halo, CN, NO₂, oxo, alkyl, cycloalkyl, alkenyl, alkynyl, aralkyl, aryl, and a heterocyclic group;
each R¹⁴ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;
q is 1 to 6:
r is 0 to 6; and
s is 0 to 6.

12. The compound of claim 11, having the formula D₃:

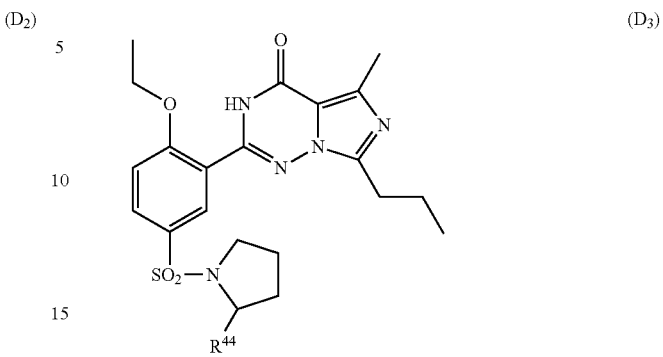

or a pharmaceutically acceptable salt, stereoisomer, or hydrate thereof, wherein
R⁴⁴ is selected from the group consisting of
—(CH₂)_q—N(R¹²)(R¹³), —(CH₂)_r—N(R¹¹)—(CH₂)_s C(O)R¹⁴, —(CH₂)_q—C(O)R¹⁴,
—(CH₂)_r—C(O)—(CH₂)_sOR¹¹, —(CH₂)_r—C(O)—(CH₂)_sN(R¹²)(R¹³), and
—(CH₂)_rO—(CH₂)_s—C(O)R¹⁴,
each R¹¹ is independently selected from H, C₃-C₆ alkyl, alkyl-O-alkyl, alkyl-O-aryl, alkenyl, alkynyl, cycloalkyl, cycloalkenyl, aralkyl, aryl and a heterocyclic group;
each R¹² and R¹³ are independently selected from H, C₂-C₆ alkyl, cycloalkyl, cycloalkenyl, alkyl-O-alkyl, alkyl-O-aryl, alkenyl, alkynyl, aralkyl, aryl and a heterocyclic group; or R¹² and R¹³ may be taken together with the nitrogen to which they are attached form a 5- to 7-membered ring which may optionally contain a further heteroatom and may be optionally substituted with up to three substituents selected from halo, CN, NO₂, oxo, alkyl, cycloalkyl, alkenyl, alkynyl, aralkyl, aryl, and a heterocyclic group;
each R¹⁴ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;
q is 1 to 6:
r is 0 to 6; and
s is 0 to 6.

13. The compound of claim 12, having a structure:

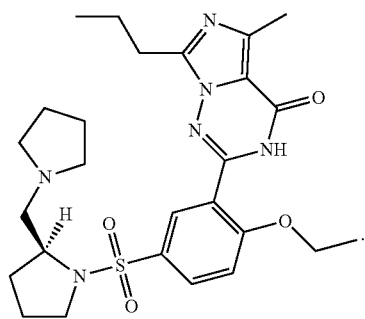 [SMILES: CCCc1nc(C)c2c(=O)[nH]c(-c3cc(S(=O)(=O)N4CCC[C@H]4CN4CCCC4)ccc3OCC)nn12]

14. The compound of claim 1, having the formula $E_1$:

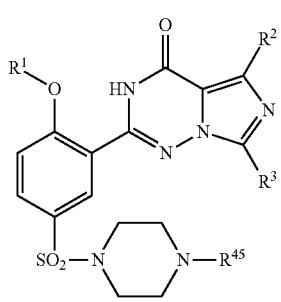

(E$_1$)

or a pharmaceutically acceptable salt, stereoisomer, or hydrate thereof, wherein $R^1$ is selected from lower alkyl;

$R^2$ is selected from lower alkyl, and lower alkenyl and lower alkynyl, wherein the lower alkyl, lower alkenyl, and lower alkynyl may be optionally substituted with one or more halogen, lower alkoxy, hydroxy, CN, NO$_2$, amino, acylamino, amido, alkylthio, and —X—C(=O)—R or —C(=O)X—R, wherein X is a bond or oxygen or sulfur and R is H, alkyl, alkenyl, alkynyl, aralkyl, aryl, or a heterocyclic group;

$R^3$ is selected from $C_1$-$C_4$ alkyl, lower alkenyl and lower alkynyl, wherein the $C_1$-$C_4$ alkyl, lower alkenyl, and lower alkynyl may be optionally substituted with one or more halogen, lower alkoxy, hydroxy, CN, NO$_2$, amino, acylamino, amido, alkylthio, and —X—C(=O)—R or —C(=O)X—R, wherein X is a bond or oxygen or sulfur and R is H, alkyl, alkynyl, aralkyl, aryl, or a heterocyclic group;

$R^{45}$ is selected from the group consisting of
—(CH$_2$)$_v$—N(R$^{25}$)(R$^{26}$), —(CH$_2$)$_v$—N(R$^{21}$)—(CH$_2$)$_w$—C(O)R$^{24}$, —(CH$_2$)$_v$—C(O)R$^{24}$,
—(CH$_2$)$_t$—C(O)—(CH$_2$)$_w$OR$^{21}$, —(CH$_2$)$_t$—C(O)(CH$_2$)$_w$—N(R$^{22}$)(R$^{23}$), and
—(CH$_2$)$_v$—O—(CH$_2$)$_w$—C(O)R$^{24}$;

each $R^{21}$ is independently selected from H, $C_5$-$C_6$ alkyl, alkyl-O-alkyl, alkyl-O-aryl, alkenyl, alkynyl, cycloalkyl, cycloalkenyl, aralkyl, aryl and a heterocyclic group;

each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group, each $R^{24}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

$R^{25}$ and $R^{26}$ taken together with the nitrogen to which they are attached form a 5- to 7-membered ring which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group;

t is 0 to 6;

v is 1 to 6; and w is 0 to 6.

15. The compound of claim 14, having the formula $E_2$:

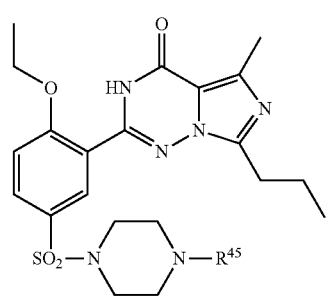

(E$_2$)

or a pharmaceutically acceptable salt, stereoisomer, or hydrate thereof, wherein $R^{45}$ is selected from the group consisting of
—(CH$_2$)$_v$—N(R$^{25}$)(R$^{26}$), —(CH$_2$)$_v$—N(R$^{21}$)—(CH$_2$)$_w$—C(O)R$^{24}$, —(CH$_2$)$_v$—C(O)R$^{24}$,
—(CH$_2$)$_t$—C(O)—(CH$_2$)$_w$OR$^{21}$, —(CH$_2$)$_t$—C(O)(CH$_2$)$_w$—N(R$^{22}$)(R$^{23}$), and
—(CH$_2$)$_v$—O—(CH$_2$)$_w$—C(O)R$^{24}$;

each $R^{21}$ is independently selected from H, $C_5$-$C_6$ alkyl, alkyl-O-alkyl, alkyl-O-aryl, alkenyl, alkynyl, cycloalkyl, cycloalkenyl, aralkyl, aryl and a heterocyclic group;

each $R^{22}$ and $R^{23}$ are independently selected from H, alkyl, cycloalkyl, cycloalkenyl, alkyl-O-alkyl, alkyl-O-aryl, alkenyl, alkynyl, aralkyl, aryl and a heterocyclic group; or $R^{22}$ and $R^{23}$ may be taken together with the nitrogen to which they are attached form a 5- to 7-membered ring which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group, each $R^{24}$ is independently selected from H, alkyl, —OH, —O-alkyl, —O-aryl, —O-aralkyl, -alkyl-O-alkyl, -alkyl-O-aryl, alkenyl, alkynyl, cycloalkyl, cycloalkenyl, aralkyl, aryl and a heterocyclic group;

$R^{25}$ and $R^{26}$ taken together with the nitrogen to which they are attached form a 5- to 7-membered ring which may optionally contain a further heteroatom and may be optionally substituted with up to three substituents selected from halo, CN, NO$_2$, oxo, alkyl, cycloalkyl, alkenyl, alkynyl, aralkyl, aryl, and a heterocyclic group;

t is 0 to 6;

v is 1 to 6; and w is 0 to 6.

16. A compound of having a structure selected from the group consisting of:
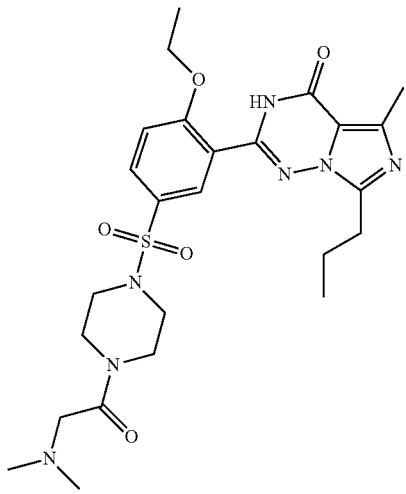
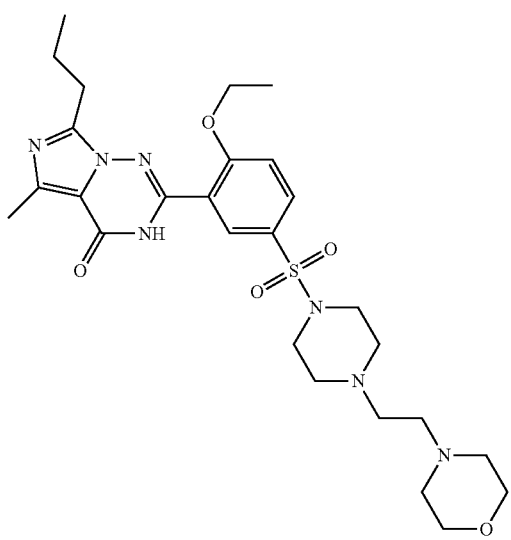
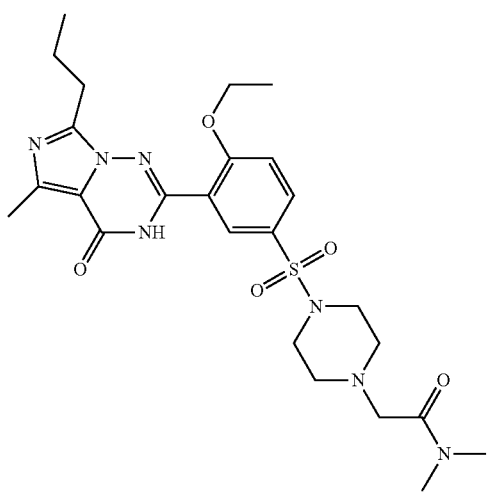
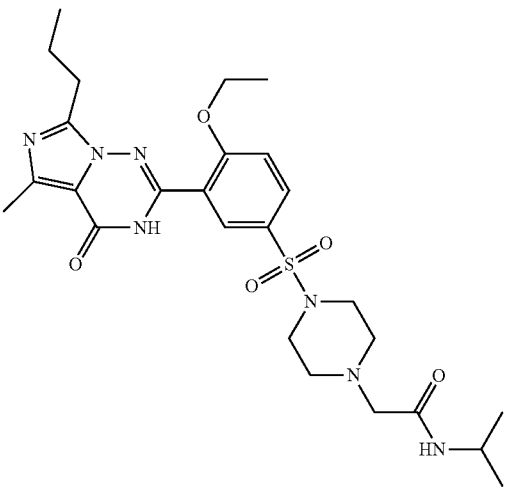
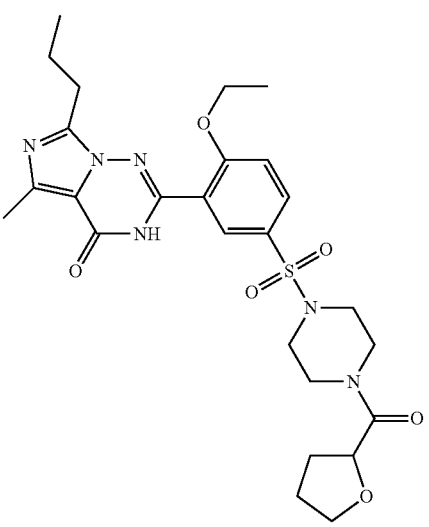
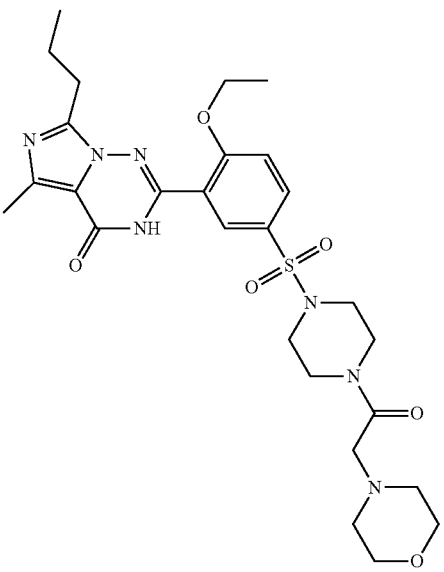

-continued

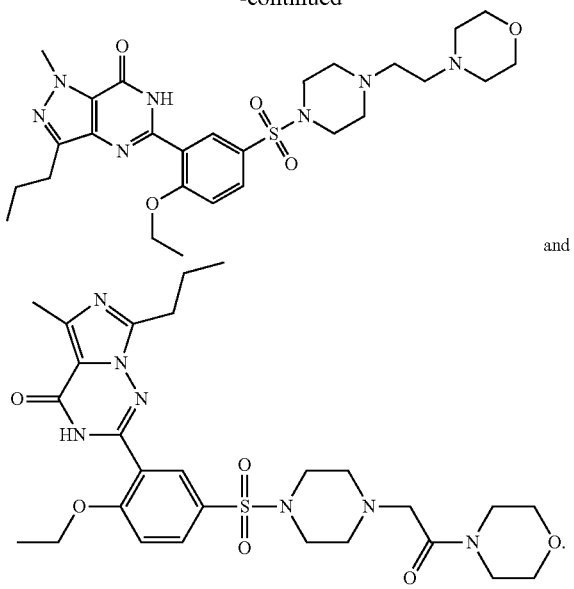

and

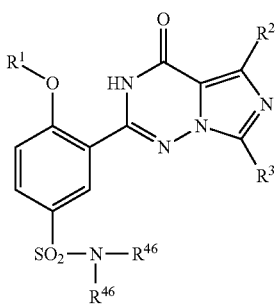

17. The compound of claim 1, having the formula:

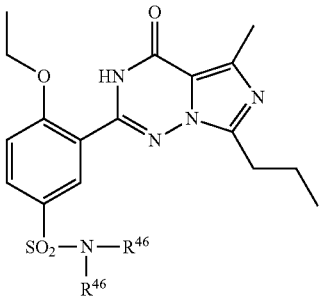

or a pharmaceutically acceptable salt, stereoisomer, or hydrate thereof, wherein
$R^1$ is selected from lower alkyl;
$R^2$ is selected from lower alkyl, and lower alkenyl and lower alkynyl, wherein the lower alkyl, lower alkenyl, and lower alkynyl may be optionally substituted with one or more halogen, lower alkoxy, hydroxy, CN, NO$_2$, amino, acylamino, amido, alkylthio, and —X—C(=O)—R or —C(=O)X—R, wherein X is a bond or oxygen or sulfur and R is H, alkyl, alkenyl, alkynyl, aralkyl, aryl, or a heterocyclic group;
$R^3$ is selected from $C_1$-$C_4$ alkyl, lower alkenyl and lower alkynyl, wherein the $C_1$-$C_4$ alkyl, lower alkenyl, and lower alkynyl may be optionally substituted with one or more halogen, lower alkoxy, hydroxy, CN, NO$_2$, amino, acylamino, amido, alkylthio, and —X—C(=O)—R or —C(=O)X—R, wherein X is a bond or oxygen or sulfur and R is H, alkyl, alkynyl, aralkyl, aryl, or a heterocyclic group; and
$R^{46}$ are both selected from $C_2$-$C_6$ alkyl-O—$C_2$-$C_6$ alkyl.

18. The compound of claim 17, having the formula:

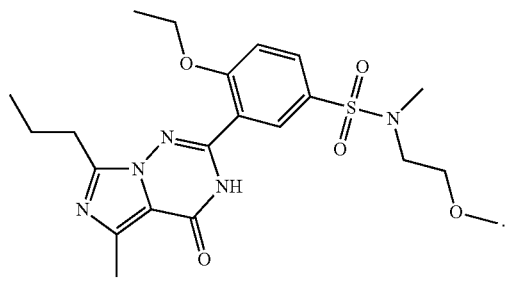 [SMILES: CCCc1nc(C)c2c(=O)[nH]c(-c3cc(S(=O)(=O)N(C)CCOC)ccc3OCC)nn12]

or a pharmaceutically acceptable salt, stereoisomer, or hydrate thereof, wherein
$R^{46}$ are both selected from $C_2$-$C_6$ alkyl-O—$C_2$-$C_6$ alkyl.

19. A method of treating erectile dysfunction comprising:
administering a therapeutically effective amount of a compound according to any one of claims 1-18 in combination with a pharmaceutically acceptable excipient to a patient suffering from erectile dysfunction.

20. A method of treating cardiovascular disorders comprising:
administering a therapeutically effective amount of a compound according to any one of claims 1-18 in combination with a pharmaceutically acceptable excipient to a patient suffering from a cardiovascular disorder.

21. The method of claim 20, wherein the cardiovascular disorder is hypertension.

22. A compound having the structure:

or a pharmaceutically acceptable salt, stereoisomer, or hydrate thereof.

23. A method of treating erectile dysfunction comprising:
administering a therapeutically effective amount of a compound according to claim 22 in combination with a pharmaceutically acceptable excipient to a patient suffering from erectile dysfunction.

24. A method of treating cardiovascular disorders comprising:
administering a therapeutically effective amount of a compound according to claim 22 in combination with a pharmaceutically acceptable excipient to a patient suffering from a cardiovascular disorder.

25. The method of claim 22, wherein the cardiovascular disorder is hypertension.

* * * * *